United States Patent
Potyrailo et al.

(10) Patent No.: US 9,538,657 B2
(45) Date of Patent: Jan. 3, 2017

(54) RESONANT SENSOR AND AN ASSOCIATED SENSING METHOD

(75) Inventors: Radislav Alexandrovich Potyrailo, Niskayuna, NY (US); Cheryl Margaret Surman, Albany, NY (US); Steven Yuehin Go, Schenectady, NY (US); Yongjae Lee, Niskayuna, NY (US)

(73) Assignee: General Electric Company, Niskayuna, NY (US)

( * ) Notice: Subject to any disclaimer, the term of this patent is extended or adjusted under 35 U.S.C. 154(b) by 970 days.

(21) Appl. No.: 13/538,570

(22) Filed: Jun. 29, 2012

(65) Prior Publication Data

US 2014/0002111 A1    Jan. 2, 2014

(51) Int. Cl.

| | |
|---|---|
| *H04Q 5/22* | (2006.01) |
| *G08B 13/14* | (2006.01) |
| *H05K 1/16* | (2006.01) |
| *G01N 27/02* | (2006.01) |
| *G01N 27/327* | (2006.01) |
| *G01N 33/487* | (2006.01) |

(52) U.S. Cl.
CPC .............. *H05K 1/16* (2013.01); *G01N 27/026* (2013.01); *G01N 27/3278* (2013.01); *G01N 33/48792* (2013.01); *H05K 2201/0338* (2013.01); *H05K 2201/09263* (2013.01); *H05K 2201/10151* (2013.01); *Y10T 29/4913* (2015.01)

(58) Field of Classification Search
CPC .............. G01R 33/543; G01R 33/4818; G01R 33/4828; G01R 33/385; G01R 27/26; G01R 27/2605; G01D 5/24; G01D 5/241; G01D 5/2412; G01D 5/2417; G06K 9/0002; H03K 17/955; H03K 2217/960725; G06F 3/0414; G06F 2203/04103; G01L 1/146

USPC .............. 324/655, 309, 315, 316, 633, 652, 668,324/675, 682, 708, 76.51, 696, 654, 658, 661,324/663, 519, 548, 662, 669, 671, 684, 76.79,324/76.81, 123 R, 123 C, 750.17; 702/47, 52; 345/174, 173
See application file for complete search history.

(56) References Cited

U.S. PATENT DOCUMENTS

| | | |
|---|---|---|
| 3,675,121 A | 7/1972 | Thompson |
| 3,778,706 A | 12/1973 | Thompson |
| 3,927,369 A | 12/1975 | Billeter et al. |
| 4,096,385 A | 6/1978 | Marett |
| 4,273,636 A | 6/1981 | Shimada et al. |
| 4,275,364 A | 6/1981 | Skatvold |

(Continued)

FOREIGN PATENT DOCUMENTS

| | | |
|---|---|---|
| CN | 1865966 A | 11/2006 |
| CN | 101022760 A | 8/2007 |

(Continued)

OTHER PUBLICATIONS

Potyrailo et al., "Selective Quantitation of Vapors and their Mixtures using Individual Passive Multivariable RFID Sensors", The 2010 IEEE International Conference on RFID, Apr. 14-16, 2010, pp. 22-28.

(Continued)

*Primary Examiner* — Patrick Assouad
*Assistant Examiner* — Taqi Nasir
(74) *Attorney, Agent, or Firm* — Joseph J. Christian

(57) ABSTRACT

A sensing system includes an inductor-capacitor-resistor (LCR) resonator sensor having a substrate, a plurality of first sensing elements mutually spaced apart and disposed on the substrate, and a sensing material film being disposed on a first sensing region of the corresponding first sensing element.

30 Claims, 16 Drawing Sheets

(56) References Cited

U.S. PATENT DOCUMENTS

| | | |
|---|---|---|
| 4,372,164 A | 2/1983 | Brown et al. |
| 4,553,434 A | 11/1985 | Spaargaren |
| 4,728,892 A | 3/1988 | Vinegar et al. |
| 4,820,989 A | 4/1989 | Vail, III |
| 4,844,097 A | 7/1989 | Bellhouse et al. |
| 4,876,512 A | 10/1989 | Kroeger et al. |
| 4,882,542 A | 11/1989 | Vail, III |
| 4,887,455 A | 12/1989 | Payne et al. |
| 4,922,745 A | 5/1990 | Rudkin et al. |
| 4,941,958 A | 7/1990 | Byers |
| 4,965,522 A | 10/1990 | Hazen et al. |
| 4,996,490 A | 2/1991 | Scott et al. |
| 5,010,301 A | 4/1991 | Leung et al. |
| 5,025,346 A | 6/1991 | Tang et al. |
| 5,059,790 A | 10/1991 | Klainer et al. |
| 5,089,780 A | 2/1992 | Megerle |
| 5,157,338 A | 10/1992 | Motherbaugh et al. |
| 5,208,165 A | 5/1993 | Law et al. |
| 5,241,364 A | 8/1993 | Kimura |
| 5,260,569 A | 11/1993 | Kimura |
| 5,344,547 A | 9/1994 | Vlasov et al. |
| 5,421,983 A | 6/1995 | Slack et al. |
| 5,443,985 A | 8/1995 | Lu et al. |
| 5,497,140 A | 3/1996 | Tuttle |
| 5,591,896 A | 1/1997 | Lin |
| 5,592,040 A | 1/1997 | Yamamoto |
| 5,607,566 A | 3/1997 | Brown et al. |
| 5,646,592 A | 7/1997 | Tuttle |
| 5,672,319 A | 9/1997 | Eisum |
| 5,744,902 A | 4/1998 | Vig |
| 5,751,475 A | 5/1998 | Ishiwata et al. |
| 5,754,055 A | 5/1998 | McAdoo et al. |
| 5,785,181 A | 7/1998 | Quartararo, Jr. |
| 5,786,595 A | 7/1998 | Herron et al. |
| 5,817,943 A | 10/1998 | Welles, II et al. |
| 5,831,439 A | 11/1998 | Suenram et al. |
| 5,840,168 A | 11/1998 | Chaniotakis et al. |
| 5,874,047 A | 2/1999 | Schoening et al. |
| 5,961,923 A | 10/1999 | Nova et al. |
| 6,025,725 A | 2/2000 | Gershenfeld et al. |
| 6,025,783 A | 2/2000 | Steffens, Jr. |
| 6,166,546 A | 12/2000 | Scheihing et al. |
| 6,189,656 B1 | 2/2001 | Morgenstern et al. |
| 6,192,753 B1 | 2/2001 | Czarnek |
| 6,204,764 B1 | 3/2001 | Maloney |
| 6,278,379 B1 | 8/2001 | Allen et al. |
| 6,287,765 B1 | 9/2001 | Cubicciotti |
| 6,359,444 B1 | 3/2002 | Grimes |
| 6,360,585 B1 | 3/2002 | Potyrailo et al. |
| 6,398,931 B1 | 6/2002 | Burchette et al. |
| 6,399,375 B2 | 6/2002 | Vajta |
| 6,406,668 B1 | 6/2002 | Dordick et al. |
| 6,461,872 B1 | 10/2002 | Sivavec et al. |
| 6,471,838 B1 | 10/2002 | Igel et al. |
| 6,506,346 B1 | 1/2003 | Monro |
| 6,532,834 B1 | 3/2003 | Pinto et al. |
| 6,544,193 B2 | 4/2003 | Abreu |
| 6,586,946 B2 | 7/2003 | Hefti et al. |
| 6,614,229 B1 | 9/2003 | Clark et al. |
| 6,657,429 B1 | 12/2003 | Goldfine et al. |
| 6,672,512 B2 | 1/2004 | Bridgelall |
| 6,676,903 B2 | 1/2004 | Potyrailo et al. |
| 6,730,201 B1 | 5/2004 | Kuhlman et al. |
| 6,751,557 B1 | 6/2004 | Shehab et al. |
| 6,771,074 B2 | 8/2004 | Zou et al. |
| 6,773,926 B1 | 8/2004 | Freund et al. |
| 6,780,307 B2 | 8/2004 | Kidwell |
| 6,782,736 B1 | 8/2004 | Hammer |
| 6,804,544 B2 | 10/2004 | Van Antwerp et al. |
| 6,818,450 B2 | 11/2004 | Eaton et al. |
| 6,864,801 B2 | 3/2005 | Tabanou et al. |
| 6,891,383 B2 | 5/2005 | Nicholson et al. |
| 6,953,520 B2 | 10/2005 | Yengoyan et al. |
| 7,017,404 B1 | 3/2006 | Kain |
| 7,031,560 B2 | 4/2006 | Lelong-Feneyrou et al. |
| 7,034,660 B2 | 4/2006 | Watters et al. |
| 7,038,470 B1 | 5/2006 | Johnson |
| 7,040,139 B2 | 5/2006 | Sunshine |
| 7,076,858 B2 | 7/2006 | Eckstein et al. |
| 7,113,125 B2 | 9/2006 | Le Sesne |
| 7,125,382 B2 | 10/2006 | Zhou et al. |
| 7,126,013 B2 | 10/2006 | Heeney et al. |
| 7,168,310 B2 | 1/2007 | Al-Ruwaili |
| 7,171,312 B2 | 1/2007 | Steinthal et al. |
| 7,178,416 B2 | 2/2007 | Whelan et al. |
| 7,204,128 B1 | 4/2007 | Liu et al. |
| 7,252,010 B2 | 8/2007 | Ohta et al. |
| 7,276,916 B2 | 10/2007 | Hammer |
| 7,293,450 B2 | 11/2007 | Liu et al. |
| 7,317,989 B2 | 1/2008 | DiFoggio et al. |
| 7,335,336 B1 | 2/2008 | Kim |
| 7,350,367 B2 | 4/2008 | Matsiev et al. |
| 7,434,457 B2 | 10/2008 | Goodwin et al. |
| 7,445,143 B2 | 11/2008 | Pang et al. |
| 7,449,893 B1 | 11/2008 | Tsironis |
| 7,455,108 B2 | 11/2008 | Jenkins et al. |
| 7,456,744 B2 | 11/2008 | Kuhns |
| 7,466,041 B2 | 12/2008 | Urman |
| 7,481,771 B2 | 1/2009 | Fonseca et al. |
| 7,483,743 B2 | 1/2009 | Mann et al. |
| 7,486,495 B1 | 2/2009 | Diederichs et al. |
| 7,495,454 B2 | 2/2009 | Rivera |
| 7,523,647 B2 | 4/2009 | Scott |
| 7,562,557 B2 | 7/2009 | Bennett et al. |
| 7,569,810 B1 | 8/2009 | Troxler et al. |
| 7,629,167 B2 | 12/2009 | Hodge et al. |
| 7,677,307 B2 | 3/2010 | Vasques et al. |
| 7,691,329 B2 | 4/2010 | Potyrailo et al. |
| 7,697,574 B2 | 4/2010 | Suematsu et al. |
| 7,808,235 B2 | 10/2010 | Rollins et al. |
| 7,812,609 B2 | 10/2010 | Martinez et al. |
| 7,911,345 B2 | 3/2011 | Potyrailo et al. |
| 7,948,380 B2 | 5/2011 | Kuhns et al. |
| 7,948,385 B2 | 5/2011 | Potyrailo et al. |
| 7,958,772 B2 | 6/2011 | Permuy et al. |
| 7,969,307 B2 | 6/2011 | Peeters |
| 8,018,342 B2 | 9/2011 | Monk et al. |
| 8,063,648 B2 | 11/2011 | Nilsson et al. |
| 8,111,143 B2 | 2/2012 | Tong et al. |
| 8,154,389 B2 | 4/2012 | Rowland et al. |
| 8,155,891 B2 | 4/2012 | Kong et al. |
| 8,159,347 B2 | 4/2012 | Potyrailo et al. |
| 8,184,290 B2 | 5/2012 | Hertens et al. |
| 8,190,394 B2 | 5/2012 | Davis et al. |
| 8,232,091 B2 | 7/2012 | Maltezos et al. |
| 8,246,910 B2 | 8/2012 | Dhirani et al. |
| 8,261,618 B2 | 9/2012 | Engle et al. |
| 8,342,242 B2 | 1/2013 | Roddy et al. |
| 8,429,985 B2 | 4/2013 | Furlong |
| 8,452,716 B2 | 5/2013 | Howley et al. |
| 8,468,871 B2 | 6/2013 | Potyrailo et al. |
| 8,547,110 B2 | 10/2013 | Kesil et al. |
| 8,643,388 B2 | 2/2014 | Hedges |
| 8,676,436 B2 | 3/2014 | Raimarckers et al. |
| 8,710,973 B2 | 4/2014 | Schneider et al. |
| 8,732,938 B2 | 5/2014 | Kolosov et al. |
| 8,833,145 B2 | 9/2014 | Fischer et al. |
| 8,933,706 B1 | 1/2015 | Karlquist |
| 8,952,708 B2 | 2/2015 | Nikolenko |
| 9,074,966 B2 | 7/2015 | Sanderlin et al. |
| 2001/0045355 A1 | 11/2001 | Gephart et al. |
| 2002/0050929 A1 | 5/2002 | Parrotta et al. |
| 2002/0081231 A1 | 6/2002 | Shapiro et al. |
| 2002/0089356 A1 | 7/2002 | Perrott et al. |
| 2002/0149466 A1 | 10/2002 | Sunshine et al. |
| 2002/0173040 A1* | 11/2002 | Potyrailo ............... G01N 33/28 436/2 |
| 2002/0177232 A1 | 11/2002 | Melker et al. |
| 2002/0197725 A1 | 12/2002 | Eaton et al. |
| 2003/0053936 A1 | 3/2003 | Potyrailo et al. |
| 2003/0154031 A1 | 8/2003 | Potyrailo et al. |
| 2003/0179024 A1 | 9/2003 | Montagnana |
| 2003/0232223 A1 | 12/2003 | Leddy et al. |
| 2004/0051154 A1 | 3/2004 | Yamakawa et al. |

(56) References Cited

U.S. PATENT DOCUMENTS

| | | |
|---|---|---|
| 2004/0113790 A1 | 6/2004 | Hamel et al. |
| 2004/0125442 A1 | 7/2004 | Yun et al. |
| 2004/0155667 A1 | 8/2004 | Kesil et al. |
| 2004/0219523 A1 | 11/2004 | Stanton et al. |
| 2004/0227682 A1 | 11/2004 | Anderson |
| 2004/0248315 A1 | 12/2004 | Klein et al. |
| 2005/0022581 A1 | 2/2005 | Sunshine |
| 2005/0058460 A1 | 3/2005 | Wang |
| 2005/0093760 A1 | 5/2005 | Rochelle et al. |
| 2005/0193832 A1 | 9/2005 | Tombs et al. |
| 2006/0014172 A1 | 1/2006 | Muller et al. |
| 2006/0020427 A1 | 1/2006 | Kahn et al. |
| 2006/0055531 A1 | 3/2006 | Cook et al. |
| 2006/0081471 A1 | 4/2006 | Kidwell |
| 2006/0133720 A1* | 6/2006 | Hochberg .......... G02B 6/12007 385/15 |
| 2006/0141469 A1 | 6/2006 | Rossier et al. |
| 2006/0198760 A1 | 9/2006 | Potyrailo et al. |
| 2006/0205093 A1 | 9/2006 | Prins |
| 2006/0210440 A1 | 9/2006 | Potyrailo et al. |
| 2006/0238349 A1 | 10/2006 | Hu et al. |
| 2006/0265150 A1 | 11/2006 | Hu et al. |
| 2007/0029195 A1 | 2/2007 | Li et al. |
| 2007/0064839 A1 | 3/2007 | Luu |
| 2007/0084277 A1 | 4/2007 | Steinsiek |
| 2007/0085686 A1 | 4/2007 | Oz |
| 2007/0090926 A1 | 4/2007 | Potyrailo et al. |
| 2007/0090927 A1* | 4/2007 | Potyrailo .......... G06K 19/0717 340/10.41 |
| 2007/0111222 A1 | 5/2007 | Chasin et al. |
| 2007/0131418 A1 | 6/2007 | Barrow et al. |
| 2007/0148670 A1 | 6/2007 | O'Malley |
| 2007/0176773 A1 | 8/2007 | Smolander et al. |
| 2007/0236338 A1 | 10/2007 | Maruyama |
| 2007/0241890 A1 | 10/2007 | Yoshioka |
| 2008/0090926 A1 | 4/2008 | Kang et al. |
| 2008/0093219 A1 | 4/2008 | Goldberg et al. |
| 2008/0116908 A1 | 5/2008 | Potyrailo et al. |
| 2008/0135614 A1 | 6/2008 | Werner et al. |
| 2008/0157901 A1 | 7/2008 | Matekovits et al. |
| 2008/0177150 A1 | 7/2008 | Il et al. |
| 2008/0179197 A1 | 7/2008 | Wu |
| 2008/0180249 A1 | 7/2008 | Butler et al. |
| 2008/0184787 A1 | 8/2008 | Coates |
| 2008/0191859 A1 | 8/2008 | Tiek et al. |
| 2008/0236814 A1 | 10/2008 | Roddy |
| 2008/0280374 A1* | 11/2008 | Potyrailo ............. G01N 21/554 436/172 |
| 2009/0035856 A1 | 2/2009 | Galliher et al. |
| 2009/0039864 A1 | 2/2009 | Gordon |
| 2009/0087862 A1 | 4/2009 | Carter et al. |
| 2009/0095073 A1 | 4/2009 | Fukumura et al. |
| 2009/0104707 A1 | 4/2009 | Wang et al. |
| 2009/0120169 A1 | 5/2009 | Chandler et al. |
| 2009/0204250 A1 | 8/2009 | Potyrailo et al. |
| 2009/0215646 A1 | 8/2009 | Anslyn et al. |
| 2009/0256679 A1 | 10/2009 | Potyrailo et al. |
| 2009/0265037 A1 | 10/2009 | Bassa |
| 2009/0289776 A1 | 11/2009 | Moore et al. |
| 2009/0289792 A1 | 11/2009 | Potyrailo et al. |
| 2009/0308155 A1 | 12/2009 | Zhang |
| 2010/0021993 A1 | 1/2010 | Wang et al. |
| 2010/0042338 A1 | 2/2010 | Giurgiutiu et al. |
| 2010/0059221 A1 | 3/2010 | Vannuffelen et al. |
| 2010/0075405 A1 | 3/2010 | Broadley |
| 2010/0134286 A1* | 6/2010 | Potyrailo ......... G06K 19/07749 340/572.1 |
| 2010/0138267 A1 | 6/2010 | Vittal et al. |
| 2010/0153323 A1 | 6/2010 | Hennessy et al. |
| 2010/0231407 A1 | 9/2010 | Carr |
| 2010/0250170 A1 | 9/2010 | Kalinin et al. |
| 2010/0261226 A1 | 10/2010 | Niazi |
| 2010/0268479 A1* | 10/2010 | Potyrailo ............. G01N 27/026 702/23 |
| 2010/0280788 A1 | 11/2010 | Bohan et al. |
| 2010/0295558 A1 | 11/2010 | Eberheim et al. |
| 2011/0006878 A1 | 1/2011 | Nyffeler et al. |
| 2011/0006900 A1 | 1/2011 | Nyffeler et al. |
| 2011/0012736 A1 | 1/2011 | Potyrailo et al. |
| 2011/0018649 A1 | 1/2011 | David et al. |
| 2011/0022318 A1 | 1/2011 | Zhao et al. |
| 2011/0029156 A1 | 2/2011 | Vernacchia et al. |
| 2011/0045601 A1 | 2/2011 | Gryska et al. |
| 2011/0051775 A1 | 3/2011 | Ivanov et al. |
| 2011/0101996 A1* | 5/2011 | Potyrailo ............... G01D 21/00 324/655 |
| 2011/0117538 A1 | 5/2011 | Niazi |
| 2011/0152706 A1 | 6/2011 | Christopherson et al. |
| 2011/0152750 A1 | 6/2011 | Dacey, Jr. et al. |
| 2011/0156177 A1 | 6/2011 | Merz |
| 2011/0160681 A1 | 6/2011 | Dacey, Jr. et al. |
| 2011/0221667 A1 | 9/2011 | Lee |
| 2011/0248825 A1 | 10/2011 | Hamel et al. |
| 2011/0263036 A1 | 10/2011 | Blauw et al. |
| 2011/0282540 A1 | 11/2011 | Armitage et al. |
| 2011/0283821 A1 | 11/2011 | Ober et al. |
| 2012/0001730 A1 | 1/2012 | Potyrailo et al. |
| 2012/0004851 A1* | 1/2012 | Potyrailo ........... G01N 33/0073 702/19 |
| 2012/0025526 A1 | 2/2012 | Luo et al. |
| 2012/0053881 A1 | 3/2012 | Schulz et al. |
| 2012/0231504 A1 | 9/2012 | Niazi |
| 2012/0258441 A1 | 10/2012 | Gebauer et al. |
| 2012/0265036 A1 | 10/2012 | Estes et al. |
| 2012/0289757 A1 | 11/2012 | Boyden et al. |
| 2013/0060112 A1 | 3/2013 | Pryor et al. |
| 2013/0182819 A1 | 7/2013 | Dvorkin et al. |
| 2013/0285677 A1 | 10/2013 | Hammer |
| 2015/0185173 A1 | 7/2015 | Potyrailo et al. |

FOREIGN PATENT DOCUMENTS

| | | |
|---|---|---|
| CN | 101057124 A | 10/2007 |
| CN | 201000455 Y | 1/2008 |
| CN | 101988574 A | 3/2011 |
| CN | 102022264 A | 4/2011 |
| CN | 102422330 A | 4/2012 |
| CN | 203923208 U | 11/2014 |
| EP | 2498076 A1 | 9/2012 |
| GB | 193953 A | 4/1958 |
| JP | 5774097 A | 5/1982 |
| JP | 59116855 U | 8/1984 |
| JP | 59160746 A | 9/1984 |
| JP | 0381659 A | 4/1991 |
| JP | 06194333 A | 7/1994 |
| JP | 6086057 U | 12/1994 |
| JP | 0773282 A | 3/1995 |
| JP | 07120423 A | 5/1995 |
| JP | 08509549 A | 10/1996 |
| JP | 09292453 A | 11/1997 |
| JP | 10504388 A | 4/1998 |
| JP | 2000111547 A | 4/2000 |
| JP | 2001502791 A | 2/2001 |
| JP | 2002125206 A | 4/2002 |
| JP | 2003503011 A | 1/2003 |
| JP | 2003506706 A | 2/2003 |
| JP | 2003161637 A | 6/2003 |
| JP | 2005156569 A | 6/2005 |
| JP | 2006516721 A | 7/2006 |
| JP | 2007516509 A | 6/2007 |
| JP | 2008129009 A | 6/2008 |
| JP | 2008236617 A | 10/2008 |
| JP | 2008298565 A | 12/2008 |
| JP | 2009092633 A | 4/2009 |
| JP | 2009538433 A | 11/2009 |
| JP | 2009540292 A | 11/2009 |
| WO | 9845779 A1 | 10/1998 |
| WO | 0055583 A1 | 9/2000 |
| WO | 0060120 A2 | 10/2000 |
| WO | 0173380 A1 | 10/2001 |
| WO | 0212129 A1 | 2/2002 |
| WO | 0223176 A1 | 3/2002 |
| WO | 03050529 A1 | 6/2003 |

(56) References Cited

FOREIGN PATENT DOCUMENTS

| WO | 2007075619 A1 | 7/2007 |
|---|---|---|
| WO | 2007101992 A1 | 9/2007 |
| WO | 2013057630 A1 | 4/2013 |
| WO | 2015090358 A1 | 6/2015 |
| WO | 2015128050 A1 | 9/2015 |

OTHER PUBLICATIONS

MacDiarmid, "Synthetic Metals: A Novel Role for Organic Polymers", Angewandte Chemie International Edition, vol. No. 40, pp. 2581-2590, 2001.

Heeger, "Semiconducting and Metallic Polymers: The Fourth Generation of Polymeric Materials", The Journal of Physical Chemistry B, vol. No. 105, Issue No. 36, pp. 8475-8491, 2001.

Mourzina et al., "Development of Multisensor Systems based on Chalcogenide Thin Film Chemical Sensors for the Simulataneous Multicomponent Analysis of Metal Ions in Complex Solutions", Electrochimica Acta, vol. No. 47, Issue No. 1-2, pp. 251-258, Sep. 1, 2001.

Gawad et al., "Micromachined Impedance Spectroscopy Flow Cytometer for Cell Analysis and Particle Sizing", Lab on a Chip, vol. No. 1, Issue No. 1, pp. 76-82, Sep. 2001.

Akyildiz et al., "Wireless Sensor Networks: A survey", Computer Networks, vol. No. 38, pp. 393-422, 2002.

Harpster et al., "A Passive Humidity Monitoring System for In-Situ Remote Wireless Testing Of Micropackages", Microelectromechanical System, vol. No. 11, Issue No. 1, pp. 61-67, 2002.

Haes et al., "A Nanoscale Optical Biosensor: Sensitivity and Selectivity of an Approach Based on the Localized Surface Plasmon Resonance Spectroscopy of Triangular Silver Nanoparticles", Journal of the American Chemical Society, vol. No. 124, Issue No. 35, pp. 10596-10604, 2002.

Janata et al., "Electrochemical Sensors and their Impedances: A Tutorial", Critical Reviews in Analytical Chemistry, vol. No. 32, Issue No. 2, pp. 109-120, 2002.

Ceresa et al., "Rational Design of Potentiometric Trace Level Ion Sensors. A Ag+-Selective Electrode with a 100 ppt Detection Limit", Analytical Chemistry, vol. No. 74, Issue No. 16, pp. 4027-4036, 2002.

Alary et al., "Subsea Water Separation: A Cost-effective Solution for Ultra Deep Water Production", 17th World Petroleum Congress, Rio de Janeiro, Brazil, Sep. 1-5, 2002.

Butler et al., "Wireless, Passive, Resonant-Circuit, Inductively Coupled, Inductive Strain Sensor", Sensors and Actuators A: Physical, vol. No. 102, Issue No. 1, pp. 61-66, Dec. 1, 2002.

Johns et al., "Sensitive Indirect Photometric Detection of Inorganic and Small Organic Anions by Capillary Electrophoresis Using Orange G as a Probe Ion", Electrophoresis, vol. No. 24, Issue No. 3, pp. 557-566, Jan. 2003.

Fauveau et al., "Guided-Wave RADAR helps Level-Detection in Harsh Settings Control Engineering", Control Engineering, vol. No. 50, Issue No. 3, pp. 16, Mar. 2003.

Grate et al., "Sorptive Behavior of Monolayer-Protected Gold Nanoparticle Films: Implications for Chemical Vapor Sensing", Analytical Chemistry, vol. No. 75, Issue No. 8, pp. 1868-1879, Apr. 15, 2003.

Grimes et al., "Resonance Sensors: A Critical Review Sensors", Analytical Chemistry, vol. No. 75, Issue No. 8, pp. 1868-1879, Apr. 15, 2003.

De Borba et al., "Determination of Sodium at Low Ng/L Concentrations in Simulated Power Plant Waters by Ion Chromatography", Journal of Chromatography, vol. No. 995, Issue No. 1-2, pp. 143-152, May 2, 2003.

Sakharov et al., "Liquid Level Sensor using Ultrasonic Lamb Waves", Ultrasonics, vol. No. 41, Issue No. 4, pp. 319-322, Jun. 2003.

Kumar et al., "Investigation into the Interaction between Surface-Bound Alkylamines and Gold Nanoparticles", Langmuir, vol. No. 19, Issue No. 15, pp. 6277-6282, 2003.

Potyrailo et al., "Fluorescence Spectroscopy and Multivariate Spectral Descriptor Analysis for High-Throughput Vlultiparameter Optimization of Polymerization Conditions of Combinatorial 96-Microreactor Arrays", Journal of Combinatorial Chemistry, vol. No. 5, Issue No. 1, pp. 8-17, 2003.

Mabic et al., "Quality Adjustment of Treated Water in an Experimental Detection", GIT Labor-Fachzeitschrift, vol. No. 47, pp. 724-727, 2003.

Pasquale, "Mechanical Sensors and Actuators", Sensors and Actuators, A: Physical, vol. No. 106, Issue No. 1-3, pp. 142-148, 2003.

Chopra et al., "Selective Gas Detection Using a Carbon Nanotube Sensor", Applied Physics Letters, vol. No. 83, pp. 2280-2282, 2003.

Janata et al., "Conducting Polymers in Electronic Chemical Sensors", Nature Materials, vol. No. 2, pp. 19-24, 2003.

Bauer et al., "Resonant Nanocluster Technology-From Optical Coding and High Quality Security Features to Biochips", Nanotechnology, vol. No. 14, Issue No. 12, pp. 1289-1311, Nov. 4, 2003.

Joseph et al., "Chemiresistor Coatings from Pt- And Au-Nanoparticle/Nonanedithiol Films: Sensitivity to Gases and Solvent Vapors", Sensors and Actuators B: Chemical, vol. No. 98, Issue No. 2-3, pp. 188-195, Mar. 15, 2004.

Shamsipur et al., "New Macrocyclic Diamides as Neutral Ionophores for Highly Selective and Sensitive PVC-Membrane Electrodes for Be2+ Ion", Electroanalysis, vol. No. 16, Issue No. 4, pp. 282-288, Mar. 2004.

Fransen, "New Control System Detects Desalter Problems before Upsets Occur", Agar Corporation, Prepared for presentation at The Aiche 2004 Spring National Meeting, Apr. 2004.

Bennett et al., "Monitoring the Operation of an Oil/Water Separator using Impedance Tomography", Minerals Engineering, vol. No. 17, Issue No. 5, pp. 605-614, May 2004.

Pavlov et al., "Aptamer-Functionalized Au Nanoparticles for the Amplified Optical Detection of Thrombin", Journal of be American Chemical Society, vol. No. 126, Issue No. 38, pp. 11768-11769, 2004.

Varma et al., "High-Speed Label-Free Detection by Spinning-Disk Micro-Interferometry", Biosensors and Bioelectronics, vol. No. 19, Issue No. 11, pp. 1371-1376, 2004.

Seyfried et al., "Measurement of Soil Water Content with a 50-MHz Soil Dielectric Sensor", Soil Science Society of America, vol. No. 68, Issue No. 2, pp. 394-403, 2004.

Want et al., "Enabling Ubiquitous Sensing with RFID", Computer, vol. No. 37, Issue No. 4, pp. 84-86, 2004.

Briglln et al., "Detection of Organic Mercaptan Vapors using Thin Films of Alkylamine-Passivated Gold Nanocrystals", Langmuir, vol. No. 20, Issue No. 2, pp. 299-305, 2004.

Ikenishi et al., "The Dielectric Characteristics of Agricultural Land for On-site and Real Time Measurement", SICE 2004 Annual Conference on, IEEE Xplore, vol. No. 2, pp. 1489-1492, Aug. 4-6, 2004.

Thomas et al., "Conjugated Polymer Sensors: Design Principles Towards Enhanced Versatility", Report No: A035334, 2 pages, Dec. 2004.

Rose et al., "Sensitivity Gains in Chemosensing by Lasing Action in Organic Polymers", Nature, vol. No. 434, pp. 376-879, Apr. 14, 2005.

Holstad et al., "Scattered Gamma Radiation Utilized for Level Measurements in Gravitational Separators", IEEE Sensors, vol. No. 5, Issue No. 2, pp. 175-182, Apr. 2005.

Cheung et al., "Impedance Spectroscopy Flow Cytometry: on-Chip Label-Free cell Differentiation", Cytometry A, vol. No. 65, Issue No. 2, pp. 124-32, Jun. 2005.

Jang et al., "Chemical Sensors Based on Highly Conductive Poly(3,4-Ethylene- Dioxythiophene) Nanorods", Advanced Materials, vol. No. 17. Issue No. 13, pp. 1616-1620, Jul. 2005.

Rakow et al., "Molecular Recognition and Discrimination of Amines with a Colorimetric Array", Angewandte Chemie, vol. No. 44, Issue No. 29, pp. 4528-4532, Jul. 18, 2005.

(56) References Cited

OTHER PUBLICATIONS

Zhang et al., "Colorimetric Sensor Array for Organics In Water", Journal of the American Chemical Society, vol. No. 127, Issue No. 33, pp. 11548-11549, 2005.
Jaworski et al., "Measurements of Oil-Water Separation Dynamics in Primary Separation Systems Using Distributed capacitance Sensors", Flow Measurement and Instrumentation, vol. No. 16, Issue No. 2-3, pp. 113-127, 2005.
Buhrdorf et al., "Multiparameteric Oil Condition Sensor Based on the Tuning Fork Technology for Automotive Applications", Book chapter in Advanced Microsystems for Automotive Applications, pp. 289-298, 2005.
Burnell et al., "Synthesis and Electrooptical Properties of Copolymers Derived from Phenol-Functionalized Telechelic Oligofluorenes", Macromolecules, vol. No. 38, Issue No. 26, pp. 10667-10677, 2005.
Chuang et al., "Embeddable Wireless Strain Sensor Based on Resonant RF Cavities", Review of Scientific Instruments, vol. No. 20, pp. 1-7, Sep. 2005.
Bang et al., "A Novel Electrochemical Detection Method for Aptamer Biosensors", Biosensors and Bioelectronics, vol. No. 21, Issue No. 6, pp. 863-870, Dec. 15, 2005.
Locklin et al., "Effect of Morphology on Organic Thin Film Transistor Sensors", Analytical and Bioanalytical Chemistry, vol. No. 384, Issue No. 2, pp. 336-342, Jan. 2006.
Meng et al., "A Multi-Electrode Capacitance Probe for Phase Detection in Oil-Water Separation Processes: Design, Modelling and Validation", Measurement Science and Technology, vol. No. 17, Issue No. 4, pp. 881-894, Mar. 2006.
Casanella et al., "Oil-water Interface Level Sensor Based on an Electrode Array", Instrumentation and Measurement Technology Coference, Sorrento, Italy, pp. 710-713, Apr. 24-27, 2006.
Lange et al., "Measuring Biomolecular Binding Events with a Compact Disc Player Device", Angewandte Chemie International Edition, vol. No. 45, pp. 270-273, 2006.
Persaud et al., "Analysis of Discrimination Mechanisms in the Mammalian Olfactory System Using a Model Nose", Mature, vol. No. 299, pp. 352-355, Sep. 23, 1982.
Sen et al., "Frequency Dependent Dielectric and Conuctivity Response of Sedimentary Rocks", Journal of Microwave Power, vol. No. 18, Issue No. 1, pp. 95-105, 1983.
Raythatha et al., "Dielectric Properties of Clay Suspensions in MHz to GHz Range", Journal of Colloid and Interface Science, vol. No. 109, Issue No. 2, pp. 301-309, Feb. 1986.
Ward et al., "In Situ Interfacial Mass Detection with Piezoelectric Transducers", Science, vol. No. 249, Issue No. 1972, pp. 1000-1007, Aug. 31, 1990.
Shi et al., "Capacitance-Based Instrumentation for Multi-Interface Level Measurement", Measurement Science and Technology, vol. No. 2, Issue No. 10, pp. 923-933, 1991.
Wise et al., "Microfabrication Techniques for Integrated Sensors and Microsystem", Science, vol. No. 254, pp. 1335-1342, 1991.
Mullen et al., "Trace Detection of Ionic Species with Surface Enhanced Raman Spectroscopy", Spectroscopy, vol. No. 7, pp. 24-32, 1992.
Ervin et al., "Development of a Fiber-Optic Sensor for Trace Metal Detection in Aqueous Environments", Applied optics, vol. No. 32, Issue No. 22, pp. 4287-4290, Aug. 1, 1993.
Agar et al., "Energy Absorption Probes Control Oily-Water Discharges", Hydrocarbon Processing, vol. No. 72, Issue No. 8, Aug. 1, 1993.
Wensink, "Dielectric Properties of Wet Soils in the Frequency Range 1-3000 MHz", Geophysical Prospecting, vol. No. 41, Issue No. 6, pp. 671-696, Aug. 1993.
Garrouch et al., "The Influence of Clay Content, Salinity, Stress, and Wettability on the Dielectric Properties of Brine-Saturated Rocks: 10 Hz to 10 MHz", Geophysics, vol. No. 59, Issue No. 6, pp. 909-917, Jun. 1994.
Pal, "Techniques for Measuring the Composition (Oil And Water Content) of Emulsions-Astate of the Art Review", Dolloids and Surfaces: A Physicochemical and Engineering Aspects, vol. No. 84, Issue No. 2-3, pp. 141-193, 1994.
Isaksen et al., "A Capacitance-Based Tomography System for Interface Measurement in Separation Vessels", Measurement Science and Technology, vol. No. 5, Issue No. 10, pp. 1262-1271, Jun. 1994.
Yang et al., "A Multi-Interface Level Measurement System using a Segmented Capacitance Sensor for Oil Separators", Measurement Science and Technology, pp. 1177-1180, Jul. 19, 1994.
Amrani et al., "High-Frequency Measurements of Conducting Polymers: Development Of A New Technique for Sensing Volatile Chemicals", http://iopscience.iop.org/0957-0233/6/101010; 8 Pages, 1995.
Legin et al "Development and Analytical Evaluation of a Multisensor System for Water Quality Monitoring", Sensors and Actuators B: Chemical, vol. No. 27, Issue No. 1-3, pp. 377-379, Jun. 1995.
Nicolaou et al., "Radiofrequency Encoded Combinatorial Chemistry", Angewandte Chemie International Edition, vol. No. 34, pp. 2289-2291, 1995.
Garcia-Golding et al., "Sensor for Determining the Water Content of Oil-in-water Emulsion by Specific Admittance Measurement", Sensors and Actuators: A. Physical, vol. No. 47, Issue No. 1-3, pp. 337-341, 1995.
Hutzler et al., "Measurement of Foam Density Profiles Using AC Capacitance", Europhysics Letters, vol. No. 31, Issue No. 8, pp. 497-502, Sep. 10, 1995.
Di Natale et al., "Multicomponent Analysis of Heavy Metal Cations and Inorganic Anions in Liquids by a Non-Selective Chalcogenide Glass Sensor Array", Sensors and Actuators B: Chemical, vol. No. 34, Issue No. 1-3, pp. 539-542, Aug. 1996.
Malinowska et al., "Enhanced Electrochemical Performance of Solid-State Ion Sensors Based on Silicone Rubber Membranes", Sensors and Actuators B: Chemical, vol. No. 43, Issue No. 1-3, pp. 161-167, Jul. 1996.
Amrani et al., "Multi-frequency Measurements of Organic Conducting Polymers for Sensing of Gases and Vapours", Sensors and Actuators B: Chemical, vol. No. 33, Issue No. 1-3, pp. 137-141, Jul. 1996.
Leff et al., "Synthesis and Characterization of Hydrophobic, Organically-Soluble Gold Nanocrystals Functionalized with Primary Amines", Langmuir, vol. No. 12, Issue No. 20, pp. 4723-4730, 1996.
Chinowski et al., "Experimental Data from a Trace Metal Sensor Combining Surface Plasmon Resonance with Anodic Stripping Voltametry", Sensors and Actuators B: Chemical, vol. No. 35, Issue No. 1-3, pp. 37-43, Sep. 1996.
Josse et al., "AC-Impedance-Based Chemical Sensors for Organic Solvent Vapors", Sensors and Actuators B: Chemical, vol. No. 36, Issue No. 1-3, pp. 363-369, Oct. 1996.
Kress-Rogers, "Handbook of Biosensors and Electronic Noses: Medicine, Food, and the Environment", CRC Press, 20 pages, Oct. 24, 1996.
Santamarina et al., "Dielectric Permittivity of Soils Mixed With Organic and Inorganic Fluids (0.02ghz to 1.30 GHz)", Journal of Environmental and Engineering Geophysics, vol. No. 2, Issue No. 1, pp. 37-52, 1997.
Hammond et al., "An Acoustic Automotive Engine Oil Quality Sensor", Solid State Sensors and Actuators, vol. 2, pp. 1343-1346, Jun. 1997.
Vlasov et al., "Cross-Sensitivity Evaluation of Chemical Sensors for Electronic Tongue: Determination of Heavy Metal Ions", Sensors and Actuators B: Chemical, vol. No. 44, Issue No. 1-3, pp. 532-537, Oct. 1997.
Di Natale et al., "Multicomponent Analysis on Polluted Waters by Means of an Electronic Tongue", Sensors and Actuators B: Chemical, vol. No. 44, Issue No. 1-3, pp. 423-428, Oct. 1997.
Ehret et al., "On-line Control of Cellular Adhesion with Impedance Measurements Using Interdigitated Electrode Structures", Medical & Biological Engineering & Computing, vol. No. 36, Issue No. 3, pp. 365-370, May 1998.
Wohltjen et al., "Colloidal Metal-Insulator-Metal Ensemble Chemiresistor", Anal.Chem, vol. No. 70, Issue No. 14, pp. 2856-2859, 1998.

(56) References Cited

OTHER PUBLICATIONS

Chyan et al., "Ultrapure Water Quality Monitoring by a Silicon-Based Potentiometric Sensor"Analyst, vol. No. 125, Issue No. 1, pp. 175-178, 1999.
Homola et al., "Surface Plasmon Resonance Sensors: Review", Sensors and Actuators B: Chemical, vol. No. 54, Issue No. 1-2, pp. 3-15, Jan. 25, 1999.
Jaworski et al., "A Capacitance Probe for Interface Detection in Oil and Gas Extraction Plant", Measurement of Science and Technology, vol. No. 10, Issue No. 3, pp. L15-L20, Jan. 1999.
Amrani et al., "Multi-Frequency Interrogation Technique Applied to Conducting Polymer Gas and Odour Sensors", vol. 146, pp. 95-101, Mar. 1999.
Schuller et al., "Advanced Profile Gauge for Multiphase Systems", 1st World Congress on Industrial Process Tomography, Buxton, Greater Manchester, Apr. 14-17, 1999.
Asskildit et al., "New Measuring Sensor for Level Detection in Subsea Separators", ABB Review, pp. 11-17, Apr. 1999.
Ishida et al., "Effects of pH on Dielectric Relaxation of Montmorillonite, Allophane, and Imogolite Suspensions, Colloid and Interface Science", ScienceDirect, vol. No. 212, Issue No. 1, pp. 152-161, Apr. 1999.
Legin et al., "The Features of the Electronic Tongue in Comparison with the Characterstics of the Discrete Ion Selective Sensor", Sensors and Actuators B: Chemical, vol. No. 58, Issue No. 1-3, pp. 464-468, Sep. 21, 1999.
Artmann, "Electronic Identification Systems: State of the Art and their Further Development", Computers and Electronics in Agriculture, vol. No. 24, Issue No. 1-2, pp. 5-26, Nov. 1999.
Jurs et al., "Computational Methods for the Analysis of Chemical Sensor Array Data from Volatile Analytes", Chemical Reviews, vol. No. 100, Issue No. 7, pp. 2649-2678, 2000.
McQuade et al., "Conjugated Polymer-Based Chemical Sensors", Chem. Rev, vol. No. 100, Issue No. 7, pp. 2537-2574, 2000.
Vlasov et al., "Electronic Tongue-New Analytical Tool for Liquid Analysis on the basis of Non-Specific Sensors and Methods of Pattern Recognition", Sensors and Actuators B: Chemical, vol. No. 65, Issue No. 1-3, pp. 235-236, Jun. 30, 2000.
Rakow et al., "A Colorimetric Sensor Array for Odour Visualization", Nature, vol. No. 406, pp. 710-713, Aug. 17, 2000.
Taton et aL., "Scanometric Dna Array Detection with Nanoparticle Probes", Science, vol. No. 289, Issue No. 5485, pp. 1757-1760, Sep. 8, 2000.
Shirakawa, "The Discovery of Polyacetylene Film: The Dawning of an Era of Conducting Polymers", Angewandte Chemie International Edition, vol. No. 40, Issue No. 14, pp. 2574-2580, Jul. 16, 2001.
Ong et al., "Design and Application of a Wireless, Passive, Resonant-Circuit Environmental Monitoring Sensor", Sensors and Actuators A: Physical, vol. No. 93, Issue No. 1, pp. 33-43, Aug. 25, 2001.
Kaya, "A Electrical Spectroscopy of Kaolin and Bentonite Slurries", Turkish Journal of Engineering and Environmental Sciences, vol. No. 25, pp. 345-354, 2001.
Lee, "Increase Oil Production and Reduce Chemical Usage through Separator Level Measurement by Density Profiling", ISA TECH/EXPO Technology Update Conference Proceedings, vol. No. 416, pp. 321-328, 2001.
Yang, "Sensors and Instrumentation for Monitoring and Control of Multi-Phase Separation", Measurement and Control, vol. No. 39, Issue No. 6, pp. 178-184, Jul. 2006.
Morris et al., "Wireless Sensor Array System for Combinatorial Screening of Sensor Materials", Combinatorial Methods and Informatics in Materials Science, vol. No. 894, pp. 219-224, 2006.
Yang et al., "Chemical Identification Using an Impedance Sensor Based on Dispersive Charge Transport", Applied Physics Letters, vol. No. 88, pp. 1-3, 2006.
Pejcic et al., "Impedance Spectroscopy: Over 35 Years of Electrochemical Sensor Optimization", Electrochimica Acta, vol. No. 51, Issue No. 28, pp. 6217-6229, Sep. 15, 2006.

Benini et al., "Wireless Sensor Networks: Enabling Technology for Ambient Intelligence", Microelectronics Journal, vol. No. 37, Issue No. 12, ppN 1639-1649, Dec. 2006.
Bai et al., "Gas Sensors Based on Conducting Polymers", Sensors (Basel), vol. No. 7, Issue No. 3, pp. 267-307, Mar. 2007.
Casanella et al., "Continuous Liquid Level Measurement Using a Linear Electrode Array", Measurement Science and Technology, vol. No. 18, Issue No. 7, pp. 178-184, May 9, 2007.
Liu et al., " Measurement of Density and Viscosity of Dodecane and Decane with a Piezoelectric Tuning Fork Over 298-448 K and 0.1-137.9 MPa", Sensors and Actuators A Physical, vol. No. 167, Issue No. 2, pp. 347-353, Jun. 2007.
Lu et al., "MEMS-Based Inductively Coupled RFID Transponder for Implantable Wireless Sensor Applications", IEEE Transactions on Magnetics, vol. No. 43, Issue No. 6, pp. 2412-2414, 2007.
Potyrailo et al., "Multianalyte Chemical Identification and Quantitation Using a Single Radio Frequency Identification Sensor", Analytical Chemistry, vol. No. 79, Issue No. 1, pp. 45-51, 2007.
Potyrailo et al., "Wireless Resonant Sensor Array for High-Throughput Screening of Materials", Review of Scientific Instruments, vol. No. 78, 2007.
Sugiyasu et al., "Conducting-Polymer-Based Chemical Sensors: Transduction Mechanisms", Bulletin of the Chemical Society of Japan, vol. No. 80, pp. 2074-2083, 2007.
Tan et al., "A Wireless, Passive Sensor for Quantifying Packaged Food Quality", Sensors, vol. No. 7, Issue No. 9, pp. 1747-1756, 2007.
Gutzeit, "Controlling Crude Unit Overhead Corrosion—Rules of Thumb for Better Crude Desalting", NACE International Corrosion Conference Series, pp. 075671-0756721, 2007.
Hua et al., "Gas sensor based conducting polymers", Sensors, vol. No. 7, pp. 267-307, 2007.
Hwang et al., "Photoelectron Spectroscopic Study of the Electronic Band Structure of Polyfluorene and Fluorene-Arylamine Copolymers at Interfaces", The Journal of Physical Chemistry C, vol. No. 111, Issue No. 3, pp. 1378-1384, 2007.
Armani et al., "Single-Molecule Detection with Optical Microcavities", Science, vol. No. 317, Issue No. 5839, pp. 183-787, Aug. 10, 2007.
Hempel et al., "5D-2 Application of a Portable Rf Impedance Spectrum Analyzer for the Investigation of Lateral Field Excited Acoustic Wave Sensors in a Liquid Environment", Ultrasonics Symposium, pp. 373-376, 2007.
Li et al., "Chemosensory Performance of Molecularly Imprinted Fluorescent Conjugated Polymer Materials", Journal of the American Chemical Society, vol. No. 129, Issue No. 51, pp. 15911-15918, 2007.
Li et al., "Inkjet Printed Chemical Sensor Array Based on Polythiophene Conductive Polymers", Sensors and Actuators 3, vol. No. 123, pp. 651-660, 2007.
Wang et al., "A New Method for On-line Monitoring of Brake Fluid Condition using an Enclosed Reference Probe", Measurement Science and Technology, vol. No. 18, Issue No. 11, pp. 3625-3635, 2007.
Wang et al., "Array of Molecularly Mediated Thin Film Assemblies of Nanoparticles: Correlation of Vapor Sensing with Interparticle Spatial Properties", Journal of the American Chemical Society, vol. No. 129, Issue No. 7, pp. 2161-2170, 2007.
Wei et al., "Simple and Sensitive Aptamer-Based Colorimetric Sensing of Protein using Unmodified Gold Nanoparticle Probes", Chemical Communications, pp. 3735-3737, 2007.
Metzger et al., "Low-cost Weight-sensitive Foam to Monitor Product Availability on Retail Shelves", International Conference on Pervasive Computing (Pervasive2007), pp. 268-279, 2007.
Hewitt, "Oil/Water Interface Control for Desalters", Petroleum Technology Quarterly 2007, vol. No. 12, Issue No. 5, pp. 75-78, 2007.
Hwili et al., "Multi-Modality Multi-Interface Level Measurement", Physics: Conference Series, vol. No. 76, Issue No. 1, pp. 1-6, 2007.
Wang et al., "A Gold Nanoparticle-Based Aptamer Target Binding Readout for ATP Assay", Advanced Materials, vol. No. 19, Issue No. 22, pp. 3943-3946, Nov. 2007.

(56) References Cited

OTHER PUBLICATIONS

Tanaka et al., "Quartz Crystal Capacitive Sensor with Inductance-Capacitance Resonance Circuit for Vapor Sensing", Japanese Journal of Applied Physics, vol. No. 46, Issue No. 11, pp. 7509-7511, Nov. 2007.
Wang et al., "Aptamer Biosensor for Protein Detection using Gold Nanoparticles", Analytical Biochemistry, vol. No. 373, Issue No. 2, pp. 213-219, Feb. 15, 2008.
Wang et al., "Electrochemical Sensors for Clinic Analysis", Sensors (Basel), vol. No. 8, Issue No. 4, pp. 2043- 2081, Apr. 2008.
Potyrailo et al., "Position-Independent Chemical Quantitation with Passive 13.56-Mhz Radio Frequency Identification (RFID) Sensors", Talanta, vol. No. 75, Issue No. 3, pp. 624-628, May 15, 2008.
Röck et al., "Electronic Nose: Current Status and Future Trends", Chemical Reviews, vol. No. 108, pp. 705-725, 2008.
Jimenez et al., "Surface Characterization of Clay Particles via Dielectric Spectroscopy", Annales Umcs, Chemistry, vol. No. 63, Issue No. 1, pp. 73-86, Jan. 2008.
Xiang-Hong et al., "Sensors and Biosensors for the Determination of Small Molecule Biological Toxins", Sensors, vol. No. 8, Issue No. 9, pp. 6045-6054, 2008.
Metzger et al., "Flexible-Foam-Based Capacitive Sensor Arrays for Object Detection at Low Cost", Applied Physics Letters, vol. No. 92, Issue No. 1, 2008.
Zheng et al., "Resonance Impedance Sensing of Human Blood Cells", Sensors and Actuators A: Physical, vol. No. 145-146, pp. 29-36, 2008.
Potyrailo et al., "Modeling of Selectivity of Multi-Analyte Response of Passive Radio Frequency Identification (RFID) Sensors", 12th International Meeting on Chemical Sensors, Columbus, 2008.
Hempel et al., "Lateral Field Excited Quartz Crystal Resonator Sensors for Determination of Acoustic and Electrical Properties of Liquids", IEEE International Frequency Control Symposium, pp. 705-710, 2008.
Potyrailo et al., "RFID Sensors based on Ubiquitous Passive 1356-MHz RFID Tags and Complex Impedance Detection", Wireless Communications and Mobile Computing, pp. 1-13, 2008.
UID, "Ultrasonic Interface Level Detector", Christian Michelsen Research, 2008.
Capone et al., "Metal Oxide Gas Sensor Array for the Detection of Diesel Fuel in Engine Oil", Sensors and Actuators B: Chemical, vol. No. 131, pp. 125-133, 2008.
Diamond et al., "Wireless Sensor Networks and Chemo-/Biosensing", Chemical Reviews, vol. No. 108, Issue No. 2 , pp. 652-679, 2008.
Hatchett et al., "Composites of Intrinsically Conducting Polymers as Sensing Nanomaterials", Chemical Reviews, vol. No. 108, Issue No. 2, pp. 746-769, 2008.
Joo et al., "Chemical Sensors with Integrated Electronics", Chemical Reviews, vol. No. 108, Issue No. 2, pp. 638-351, 2008.
Kauffman et al., "Carbon Nanotube Gas and Vapor Sensors", Angewandte Chemie International Edition, vol. No. 47, pp. 6550-6570, 2008.
Li et al., "Chemical Sensing Using Nanostructured Polythiophene Transistors", Nano Letters, vol. No. 8, Issue No. 11, pp. 3563-3567, 2008.
Palacios et al., "Rational Design of a Minimal Size Sensor Array for Metal Ion Detection", Journal of the American Chemical Society, vol. No. 130, Issue No. 31, pp. 10307-10314, 2008.
Hwili et al., "A Single Rod Multi-Modality Multi-Interface Level Sensor using an AC Current Source", IEEE International Workshop on Imaging Systems and Techniques, Sep. 10-12, 2008.
Guan et al., "Engine Lubricating Oil Classification by SAE Grade and Source Based on Dielectric Spectroscopy Data", Analytica Chimica Acta, vol. No. 628, Issue No. 1, pp. 117-120, Oct. 17, 2008.
Saltas et al., "Dielectric Properties of Non-Swelling Bentonite: The Effect of Temperature and Water Saturation", Journal of Non-Crystalline Solids, vol. No. 354, Issue No. 52-54, pp. 5533-5541, Dec. 15, 2008.

US Non-Final Rejection issued in connection with corresponding U.S. Appl. No. 12/977,599 on Feb. 5, 2013.
US Final Rejection issued in connection with corresponding U.S. Appl. No. 12/824,436 on Feb. 6, 2013.
US Non-Final Rejection issued in connection with corresponding U.S. Appl. No. 12/942,732 on Feb. 7, 2013.
De Souza et al., "A Close Dielectric Spectroscopic Analysis of Diesel/Biodiesel Blends and Potential Dielectric Approaches for Biodiesel Content Assessment", Fuel, vol. No. 105, pp. 705-710, Mar. 2013.
Swiech et al., "Dielectric Properties of Synthetic Oil Sands", Society of Petroleum Engineers—SPE Heavy Oil aonference Canada, vol. No. 1, pp. 238-248, 2013.
Zhu et al., "Survey of Lubrication Oil Condition Monitoring, Diagnostics, and Prognostics Techniques and Systems", Journal of Chemical Science and Technology, vol. No. 2, Issue No. 3, pp. 100-115, Jul. 2013.
US Final Rejection issued in connection with corresponding U.S. Appl. No. 12/325,653 on Aug. 8, 2013.
Unofficial English Translation of Japanese Office Action issued in connection with corresponding JP Application No. 2011-538590 on Oct. 8, 2013.
PCT Search Report and Written Opinion issued in connection with corresponding PCT Application No. PCT/SE2013/050671 on Nov. 18, 2013.
PCT Search Report and Written Opinion issued in connection with corresponding PCT Application No. PCT/US2013/058932 on Dec. 12, 2013.
PCT Search Report and Written Opinion issued in connection with corresponding PCT Application No. PCT/US2013/058898 on Dec. 18, 2013.
Unofficial English Translation of Chinese Office Action issued in connection with corresponding CN Application No. 201180031959.6 on Dec. 26, 2013.
US Non-Final Rejection issued in connection with corresponding U.S. Appl. No. 12/977,568 on Jan. 16, 2014.
PCT Search Report and Written Opinion issued in connection with corresponding PCT Application No. PCT/US2013/055983 on Jan. 27, 2014.
US Non-Final Rejection issued in connection with corresponding U.S. Appl. No. 12/827,623 on Jan. 30, 2014.
European Search Report and Opinion issued in connection with corresponding EP Application No. 11801238.4 on Mar. 5, 2014.
US Non-Final Rejection issued in connection with corresponding U.S. Appl. No. 12/325,653 on Mar. 17, 2014.
PCT Search Report and Written Opinion issued in connection with corresponding PCT Application No. PCT/SE2013/051590 on May 6, 2014.
PCT Search Report and Written Opinion issued in connection with corresponding PCT Application No. PCT/SE2013/051589 on May 6, 2014.
US Non-Final Rejection issued in connection with corresponding U.S. Appl. No. 13/630,939 on Aug. 11,2014.
US Non-Final Rejection issued in connection with corresponding U.S. Appl. No. 14/031,965 on Aug. 26, 2014.
Soleimani et al., "Base Oil Oxidation Detection using Novel Chemical Sensors and Impedance Spectroscopy Measurements", Sensors and Actuators B: Chemical, vol. No. 199, pp. 247-258, Aug. 2014.
US Non-Final Rejection issued in connection with corresponding U.S. Appl. No. 14/031,951 on Sep. 2, 2014.
US Final Rejection issued in connection with corresponding U.S. Appl. No. 12/325,653 on Sep. 12, 2014.
Toledo et al., "Application of Quartz Tuning Forks and Extensional Microresonators for Viscosity and Density Measurements in Oil/Fuel Mixtures", Microsystem Technologies, vol. No. 20, Issue No. 4, pp. 945-953, 2014.
US Non-Final Rejection issued in connection with corresponding U.S. Appl. No. 13/484,674 on Nov. 3, 2014.
US Non-Final Rejection issued in connection with corresponding U.S. Appl. No. 13/558,499 on Dec. 4, 2014.
US Non-Final Rejection issued in connection with corresponding U.S. Appl. No. 13/630,954 on Dec. 15, 2014.

(56) References Cited

OTHER PUBLICATIONS

US Non-Final Rejection issued in connection with corresponding U.S. Appl. No. 13/729,800 on Dec. 19, 2014.
US Final Rejection issued in connection with corresponding U.S. Appl. No. 13/630,939 on Jan. 28, 2015.
US Non-Final Rejection issued in connection with corresponding U.S. Appl. No. 13/630,739 on Feb. 25, 2015.
Unofficial English Translation of Chinese Office Action issued in connection with corresponding CN Application No. 201180032850.4 on Mar. 2, 2015.
Unofficial English Translation of Japanese Office Action issued in connection with corresponding JP Application No. 2013518325 on Mar. 24, 2015.
Unofficial English Translation of Chinese Office Action issued in connection with corresponding CN Application No. 201110461799.0 on Mar. 30, 2015.
Zhu et al.,"An Integrated Lubricant Oil Conditioning Sensor Using Signal Multiplexing", Journal of Micromechanics and Micro engineering, vol. No. 25, Issue No. 1, pp. 1-12, 2015.
Unofficial English Translation of Japanese Office Action issued in connection with corresponding JP Application No. 2013-518328 on Apr. 7, 2015.
US Non-Final Rejection issued in connection with corresponding U.S. Appl. No. 13/729,851 on Apr. 28, 2015.
A copy of US Non-Final Rejection issued in connection with corresponding U.S. Appl. No. 13/630,587 on Jun. 2, 2015.
US Final Rejection issued in connection with corresponding U.S. Appl. No. 13/630,739 on Jun. 4, 2015.
US Non-Final Rejection issued in connection with corresponding U.S. Appl. No. 13/838,884 on Jun. 17, 2015.
PCT Search Report and Written Opinion issued in connection with corresponding PCT Application No. PCT/US2015/027482 on Jul. 15, 2015.
Unofficial English Translation of Japanese Notice of Allowance issued in connection with corresponding JP Application No. 2011-258627 on Aug. 4, 2015.
Taiwan Office Action issued in connection with corresponding TW Application No. 100146015 on Aug. 6, 2015.
US Non-Final Rejection issued in connection with corresponding U.S. Appl. No. 13/630,939 on Sep. 14, 2015.
Unofficial English Translation of Japanese Grant of Patent issued in connection with corresponding JP Application No. 2013518325 on Sep. 15, 2015.
European Search Report and Opinion issued in connection with corresponding EP Application No. 11801234.3 on Oct. 28, 2015.
Unofficial English Translation of Chinese Office Action issued in connection with corresponding CN Application No. 201380043615.6 on Nov. 9, 2015.
US Non-Final Rejection issued in connection with corresponding U.S. Appl. No. 12/824,436 on Dec. 2, 2015.
MISRA, "Guide to Wireless Sensor Networks", Computer Communications and Networks, Jan. 1, 2009.
Ertl et al., "Interdigitated Impedance Sensors for Analysis of Biological Cells in Microfluidic Biochips", E & I Elektrotechnik and Informationstechnik, vol. No. 126, Issue No. 1, pp. 47-50, Feb. 2009.
Potyrailo et al., "Selective Detection of Chemical Species in Liquids and Gases using Passive Radio-Frequency Identification (RFID) Sensors", Proc. Transducers, pp. 1650-1653, 2009.
McCann et al., "Recent Advances in Lateral Field Excited and Monolithic Spiral Coil Acoustic Transduction Bulk Acoustic Wave Sensor Platforms", Measurement Science and Technology, vol. No. 20, Issue No. 12, 2009.
Sweden Office Action issued in connection with corresponding SE Application No. 0702495-3 on Jan. 26, 2009.
Potyrailo et al., "Development of Radio-Frequency Identification Sensors Based on Organic Electronic Sensing Materials for Selective Detection of Toxic Vapors", Journal of Applied Physics, vol. No. 106, Issue No. 12, pp. 124902-1 to124902-6, 2009.

Jaworski et al., "On-line Measurement of Separation Dynamics in Primary Gas/Oil/Water Separators: Challenges and Technical Solutions-A review", Petroleum Science and Engineering, vol. No. 68, pp. 47-59, 2009.
Potyrailo et al., "Combinatorial Screening of Polymeric Sensing Materials Using RFID Sensors",Journal of Combinatorial Chemistry, vol. No. 11, Issue No. 4, pp. 598-603, 2009.
Westafer et al., "Functionalization of High Frequency SAW RFID Devices for Ozone Dosimetry", IEEE Sensors, pp. 1747-1752, Oct. 25-28, 2009.
Sweden Office Action issued in connection with corresponding SE Application No. 0702495-3 on Sep. 29, 2009.
PCT Search Report and Written Opinion issued in connection with corresponding PCT Application No. PCT/SE2009/051346 on Mar. 15, 2010.
US Non-Final Rejection issued in connection with corresponding U.S. Appl. No. 11/560,476 on Apr. 5, 2010.
Potyrailo et al. "Integration of Passive Multivariable RFID Sensors into Single-Use Biopharmaceutical Manufacturing Components", RFID, 2010 IEEE International, pp. 1-7, Apr. 2010.
Becher et al., "The Detection of Evaporating Hazardous Material Released from Moving Sources Using a Gas Sensor Network", Sensors and Actuators B: Chemical, vol. No. 146, Issue No. 2, pp. 513-520, Apr. 29, 2010.
Hong et al., "Development of a Micro Liquid-Level Sensor for Harsh Environments using a Periodic Heating Technique", Measurement Science and Technology, vol. No. 21, Issue No. 10, 2010.
Potyrailo et al., "Passive Radio Frequency Identification (RFID) Chemical Sensors for Homeland Security Applications", In Wiley Handbook of Science and Technology for Homeland Security, vol. No. 1, pp. 523-544, 2010.
Wang et al., "Flexible Chemiresistor Sensors: Thin film Assemblies of Nanoparticles on a Polyethylene Terephthalate Substrate", Journal of Materials Chemistry, vol. No. 20, pp. 907-915, 2010.
Alexander et al., "Optimization of Interdigitated Electrode (IDE) Arrays for Impedance Based Evaluation of Hs 578T cancer Cells", Journal of Physics: Conference Series, vol. No. 24, Issue No. 1, pp. 1-4, 2010.
Bobrov et al., "The Effect of Clay and Organic Matter Content on the Dielectric Permittivity of Soils and Grounds at the Frequency Range from 10 MHz to 1 GHz", International Geoscience and Remote Sensing Symposium (IGARSS), pp. 4433-4435, Jul. 25-30, 2010.
Chen et al., "Based on ZigBee Wireless Sensor Network the Monitoring System Design for Production Process Toxic and Harmful Gas", International Conference on Computer, Mechatronics, Control and Electronic Engineering, vol. No. 4, pp. 425-428, 2010.
Cho et al., "Capacitive Sensor for Automotive Engine Oil Degradation using Wireless Network", International Symposium on Advanced Packaging Materials: Microtech, APM '10 , pp. 88-91, 2010.
De Vito et al., "Wireless Sensor Networks for Distributed Chemical Sensing: Addressing Power Consumption Limits with On-Board Intelligence", IEEE Sensors Journal, vol. No. 11, Issue No. 14, pp. 947-955, 2010.
Bianchi et al., "Model of an Interdigitated Microsensor to Detect and Quantify Cells Flowing in a Test Chamber", 6th annual COMSOL Conference Paris, pp. 1-5, Nov. 2010.
Suresh et al., "Piezoelectric Based Resonant Mass Sensor using Phase Measurement", Measurement, vol. No. 44, Issue No. 2, pp. 320-325, Feb. 2011.
Perez et al., "Low-Cost Oil Quality Sensor Based on Changes in Complex Permittivity", Sensors, vol. No. 11, pp. 10675-10690, 2011.
Potyrailo et al. "RFID Sensors as the Common Sensing Platform for Single-Use Biopharmaceutical Manufacturing", Measurement Science and Technology, vol. No. 22, 2011.
Potyrailo et al., "Passive Multivariable Temperature and Conductivity RFID Sensors for Single-Use Biopharmaceutical Manufacturing Components", Biotechnology Progress, vol. No. 27, Issue No. 3, pp. 875-884, May 2011.
Owenier et al., "Dielectric Permittivity of Geologic Materials at Different Water Contents—Measurements with an Impedance Ana-

(56) References Cited

OTHER PUBLICATIONS lyzer", 6th International Workshop on Advanced Ground Penetrating Radar (IWAGPR), pp. 1-5, Jun. 22-24, 2011.

Potyrailo et al., "Multivariable Passive RFID Vapor Sensors: Pilot-Scale Manufacturing and Laboratory Evaluation", IEEE International Conference on RFID, Poster 52, 2011.

US Non-Final Rejection issued in connection with corresponding U.S. Appl. No. 12/424,016 on Jul. 12, 2011.

Guan et al.,"Application of Dielectric Spectroscopy for Engine Lubricating Oil Degradation Monitoring", Sensors and Actuators A: Physical, vol. No. 168, Issue No. 1, pp. 22-29, Jul. 2011.

Wang et al., "Impedance Analysis for Lateral Field Excited Acoustic Wave Sensors", Sensors and Actuators B: chemical, vol. No. 156, Issue No. 2, pp. 969-975, Aug. 2011.

Sen et al., "Evaluation of Sensor Arrays for Engine Oils Using Artificial Oil Alteration", Proceedings of SPIE 8066, Smart Sensors Actuators and MEMS V, 2011.

Latif et al., "Conductometric Sensors for Monitoring Degradation of Automotive Engine Oil", Sensors, vol. No. 11, Issue No. 9, pp. 8611-8625, Sep. 2011.

PCT Search Report and Written Opinion issued in connection with corresponding PCT Application No. PCT/SE2011/050748 on Oct. 5, 2011.

PCT Search Report and Written Opinion issued in connection with corresponding PCT Application No. PCT/SE2011/050818 on Oct. 24, 2011.

Potyrailo et al., "Materials and Transducers Toward Selective Wireless Gas Sensing", Chemical Reviews, vol. No. 111, Issue No. 11, pp. 7315-7354, Nov. 9, 2011.

Datla et al., "Wireless Distributed Computing: A Survey of Research Challenges", IEEE Communications Magazine, vol. No. 50, Issue No. 1, pp. 144-152, Jan. 2012.

Combined GB Search and Examination Report issued in connection with corresponding GB Application No. GB1121548.0 on Mar. 28, 2012.

Vasilyeva et al., "Differences in Behaviour of Adsorbed Water in Kaolinites and Montmorillonites in Temperature Range from -90°C to +140°C by Dielectric Spectroscopy", Physics: Conference Series, vol. No. 394, Issue No. 1, pp. 1-6, 2012.

Aghayan, "On-Line Monitoring of Engine Health through the Analysis of Contaminants in Engine Lubricant", The School of Graduate and Postdoctoral Studies the University of Western Ontario London, Ontario, Canada, pp. 1-273, 2012.

US Non-Final Rejection issued in connection with corresponding U.S. Appl. No. 12/824,436 on Aug. 8, 2012.

Fochtmann et al., "Optimization of the Lateral Field Excited Platform for Liquid Sensing Applications", Sensors and Actuators B: Chemical, vol. No. 170, pp. 95-103, Jul. 1, 2012.

US Non-Final Rejection issued in connection with corresponding U.S. Appl. No. 11/560,476 on Jul. 5, 2012.

Datla et al., "Wireless Distributed Computing in Cognitive Radio Networks", Ad Hoc Networks, vol. No. 10, Issue No. 05, pp. 845-857, Jul. 2012.

Unofficial English Translation of Japanese Office Action issued in connection with corresponding Jp Application No. 2007291481 on Aug. 7, 2012.

US Non-Final Rejection issued in connection with corresponding U.S. Appl. No. 13/331,003 on Sep. 10, 2012.

US Notice of Allowance issued in connection with corresponding U.S. Appl. No. 12/424,016 on Sep. 28, 2012.

Chinese Office Action issued in connection with corresponding CN Application No. 200980149087.6 on Sep. 13, 2012.

US Non-Final Rejection issued in connection with corresponding U.S. Appl. No. 12/325,653 on Nov. 16, 2012.

Bauerle, "Study of Solid Electrolyte Polarization by a Complex Admittance Method", Journal of Physics and Chemistry of Solids, vol. No. 30, Issue No. 12, pp. 2657-2670, Dec. 1969.

Matsui, "Complex-Impedance Analysis for the Development of Zirconia Oxygen Sensors", Solid State Ionics, vol. No. 3-4, pp. 525-529, Aug. 1981.

Gutierrez et al., "Use of Complex Impedance Spectroscopy in Chemical Sensor Characterization", Sensors and Actuators B: Chemical, vol. No. 4, Issue No. 3-4, pp. 359-363, Jun. 1991.

Ghiotti et al., "Mositure Effects on Pure and Pd-Doped SnO2 Thick Films Analysed by FTIR Spectroscopy and Conductance Measurements", Sensors and Actuators B: Chemical, vol. No. 25, Issue No. 1-3, pp. 520-524, Apr. 1995.

Wang et al., "The Application of A.C. Impedance Technique for Detecting Glycol Contamination in Engine Oil", Sensors and Actuators B: Chemical, vol. No. 40, Issue No. 2-3, pp. 193-197, May 15, 1997.

Amrani et al., "An Intelligent Gas Sensing System", Sensors and Actuators B: Chemical, vol. No. 44, Issue No. 1-3, pp. 512-516, Oct. 1997.

Basu et al., "Smart Sensing" of Oil Degradation and Oil Level Measurements in Gasoline Engines, SAE 2000 World Congress, Detroit, Michigan, 2000-01-1366, pp. 1-7, Mar. 6-9, 2000.

Foster et al., "Detection of Trace Levels of Water in Oil by Photoacoustic Spectrocopy", Sensors and Actuators B: Chemical, vol. No. 77, Issue No. 3, pp. 620-624, Jul. 10, 2001.

Foster-Mills et al., "Photoacoustic Spectroscopy Detects Water in Oil", Sensors Online, pp. 1-5, Oct. 2001, Retrieved from http://archives.sensorsmag.com/articles/1001/12/pf_main.shtml on Apr. 11, 2016.

Grimes et al., "Wireless Magnetoelastic Resonance Sensors: A Critical Review", vol. No. 2, Issue No. 7, pp. 294-313, Jul. 23, 2002.

Smiechowski et al., "Electrochemical Monitoring of Water-Surfactant Interactions in Industrial Lubricants", Journal of Electroanalytical Chemistry, vol. No. 534, Issue No. 2, pp. 171-180, Oct. 18, 2002.

Finkenzeller, "RFID Handbook: Fundamentals and Applications in Contactless Smart Cards and Identification", John Wiley & Sons, Ltd, Second Edition, pp. 1-427, Jul. 21, 2003.

Wang et al., "A New Technique for Detecting Antifreeze in Engine Oil During Early Stage of Leakage", Sensors and Actuators B: Chemical, vol. No. 96, Issue No. 1-2, pp. 157-164, Nov. 15, 2003.

Barsoukov et al., "Impedance Spectroscopy: Thoery, Experiment, and Applications", Second Edition, pp. 205-264, 2005.

Lvovich et al., "Impedance Characterization of Industrial Lubricants", Electrochimica Acta, vol. No. 51, Issue No. 8-9, pp. 1487-1496, Jan. 20, 2006.

Qing et al., "RFID Tag Antennas", Antennas for Portable Devices, John Wiley & Sons, Ltd, pp. 59-61; 65-69, Mar. 2007.

Ulrich et al., "Simultaneous Estimation of Soot and Diesel Contamination in Engine Oil Using Electrochemical Impedance Spectroscopy", Sensors and Actuators B: Chemical, vol. No. 127, Issue No. 2, pp. 613-618, Nov. 15, 2007.

Surman et al., "Quantitation of Toxic Vapors in Variable Humidity Atmosphere Using Individual Passive Radio Frequency Identification (RFID) Sensors", 12th International Meeting on Chemical Sensors, Columbus, pp. 1-2, 2008.

Agoston et al., "A Concept of an Infrared Sensor System for Oil Condition Monitoring", Elektrotechnik & Informationstechnik, vol. No. 125, Issue No. 3, pp. 71-75, Mar. 2008.

Wudy et al., "Rapid Impedance Scanning QCM for Electrochemical Applications Based on Miniaturized Hardware and High-Performance Curve Fiting", Electrochimica Acta, vol. No. 53, Issue No. 22, pp. 6568-6574, Sep. 20, 2008.

Sacristan-Riquelme et al., "Low Power Impedance Measurement Integrated Circuit for Sensor Applications", Microelectronics Journal, vol. No. 40, Issue No. 1, pp. 177-184, Jan. 2009.

Niedermayer et al., "Yet Another Precision Impedance Analyzer (YAPIA)—Readout Electronics for Resonating Sensors", Sensors and Actuators A: Phsyical, vol. No. 156, Issue No. 1, pp. 245-250, Nov. 2009.

Mortier et al., "Chemistry and Technology of Lubricants", Third Edition, Springer, pp. 1-560, 2010.

Potyrailo et al., "Multivariable MHz and GHz Wireless Chem/Bio Sensors for Environmental, Industrial, and Security Applications", The 14th International Meeting on Chemical Sensors, Nuremberg, Germany, pp. 399-402, May 20-23, 2012.

(56) References Cited

OTHER PUBLICATIONS

Agilent Impedance Measurement Handbook, "A Guide to Measurement Technology and Techniques", 4th Edition, Agilent Technologies, pp. 1-140, Sep. 10, 2013.
Elzagzoug et al., "Condition Monitoring of High Voltage Transformer Oils Using Optical Chromaticity", Measurement Science and Technology, vol. No. 25, Issue No. 6, pp. 1-9, Jun. 2014.
US Non-Final Office Action issued in connection with related U.S. Appl. No. 13/331,003 on Sep. 10, 2014.
Hoja et al., "Miniaturized Impedance Analyzer Using AD5933", Lecture Notes on Impedance Spectroscopy, vol. No. 5, pp. 93-100, Feb. 17, 2015.
Chabowski et al., "Simple Wide Frequency Range Impedance Meter Based on AD5933 Integrated Circuit", Metrology and Measurement Systems, vol. No. 22, Issue No. 1, pp. 13-24, Mar. 15, 2015.
Simic, "Complex Impedance Measurement System for the Frequency Range from 5 kHz to 100 kHz", Key Engineering Materials, vol. No. 644, pp. 133-136, May 11, 2015.
Chen et al., "Novel Undercoupled Radio-Frequency (RF) Resonant Sensor for Gaseous Ethanol and Interferents Detection", Sensors and Actuators A: Physical, vol. No. 230, pp. 63-73, Jul. 1, 2015.
Ghaffari et al., "A Wireless Multi-Sensor Dielectric Impedance Spectroscopy Platform", Sensors, vol. No. 15, Issue No. 9, pp. 23575-23588, Sep. 17, 2015.
Wang et al., "Probe Improvement of Inductive Sensor for Online Health Monitoring of Mechanical Transmission Systems", IEEE Transactions on Magnetics, vol. No. 51, Issue No. 11, pp. 1-4, Nov. 2015.
Poseidon Systems, "Oil Quality Products", Trident QM1100; Trident QM2100; Trident WM800, pp. 1-3, Retrieved from http://www.poseidonsys.com/products/oil-quality on Dec. 24, 2015.
Tandelta Systems, "Oil Quality Sensor", Tandelta Oil Condition Monitoring, pp. 1-5, Retrieved from http://www.tandeltasystems.com/products/oil-quality-sensor-2/ on Dec. 24, 2015.
Unofficial English Translation of Chinese Office Action issued in connection with related CN Application No. 201380050788.0 on Jan. 20, 2016.
PCT Search Report issued in connection with related PCT Application No. PCT/EP2015/075026 on Feb. 1, 2016.
AU Examination Report issued in connection with corresponding AU Application No. 2013305814 on Jun. 10, 2016.
Eurasian Search Report issued in connection with related EA Application No. 201592216 on Aug. 4, 2016.
US Ex Parte Quayle Action issued in connection with related U.S. Appl. No. 14/532,168 on Aug. 4, 2016.
US Non-Final Office Action issued in connection with related U.S. Appl. No. 12/824,436 on Sep. 6, 2016.
U.S. Appl. No. 14/869,038, filed Sep. 29, 2015, Bret Dwayne Worden et al.
U.S. Appl. No. 14/866,320, filed Sep. 25, 2015, Radislav Alexandrovich Potyrailo et al.
U.S. Appl. No. 14/585,690, filed Dec. 30, 2014, Radislav Alexandrovich Potyrailo et al.
U.S. Appl. No. 61/987,853, filed May 2, 2014, Cheryl Margaret Surman et al.
U.S. Appl. No. 62/271,030, filed Dec. 22, 2015, Cheryl Margaret Surman et al.
U.S. Appl. No. 14/697,086, filed Apr. 27, 2015, Cheryl Margaret Surman et al.
U.S. Appl. No. 11/560,476, filed Nov. 16, 2006, Radislav Alexandrovich Potyrailo et al.
U.S. Appl. No. 12/325,653, filed Dec. 1, 2008, Radislav Alexandrovich Potyrailo et al.
U.S. Appl. No. 12/824,436, filed Jun. 28, 2010, Cheryl Margaret Surman et al.
U.S. Appl. No. 12/827,623, filed Jun. 30, 2010, Radislav Alexandrovich Potyrailo et al.
U.S. Appl. No. 12/977,568, filed Dec. 23, 2010, Radislav Alexandrovich Potyrailo et al.
U.S. Appl. No. 13/331,003, filed Dec. 20, 2011, Radislav Alexandrovich Potyrailo et al.
U.S. Appl. No. 12/424,016, filed Apr. 15, 2009, Radislav Alexandrovich Potyrailo et al.
U.S. Appl. No. 14/710,299, filed May 12, 2015, Radislav Alexandrovich Potyrailo et al.
U.S. Appl. No. 13/558,499, filed Jul. 26, 2012, Radislav Alexandrovich Potyrailo et al.
U.S. Appl. No. 13/630,939, filed Sep. 28, 2012, Radislav Alexandrovich Potyrailo et al.
U.S. Appl. No. 13/630,587, filed Sep. 28, 2012, Cheryl Margaret Surman et al.
U.S. Appl. No. 13/630,739, filed Sep. 28, 2012, Cheryl Margaret Surman et al.
U.S. Appl. No. 13/729,800, filed Dec. 28, 2012, Radislav Alexandrovich Potyrailo et al.
U.S. Appl. No. 13/729,851, filed Dec. 28, 2012, Radislav Alexandrovich Potyrailo et al.
U.S. Appl. No. 14/421,245, filed Feb. 12, 2015, Bret Dwayne Worden et al.
U.S. Appl. No. 12/977,599, filed Dec. 23, 2010, Radislav Alexandrovich Potyrailo et al.
U.S. Appl. No. 14/532,168, filed Nov. 4, 2014, Radislav Alexandrovich Potyrailo.
U.S. Appl. No. 15/060,193, filed Mar. 3, 2016, Radislav Alexandrovich Potyrailo et al.
U.S. Appl. No. 15/175,127, filed Jun. 7, 2016, Radislav Alexandrovich Potyrailo et al.
U.S. Appl. No. 29/548,993, filed Dec. 18, 2015, Bret Worden et al.

\* cited by examiner

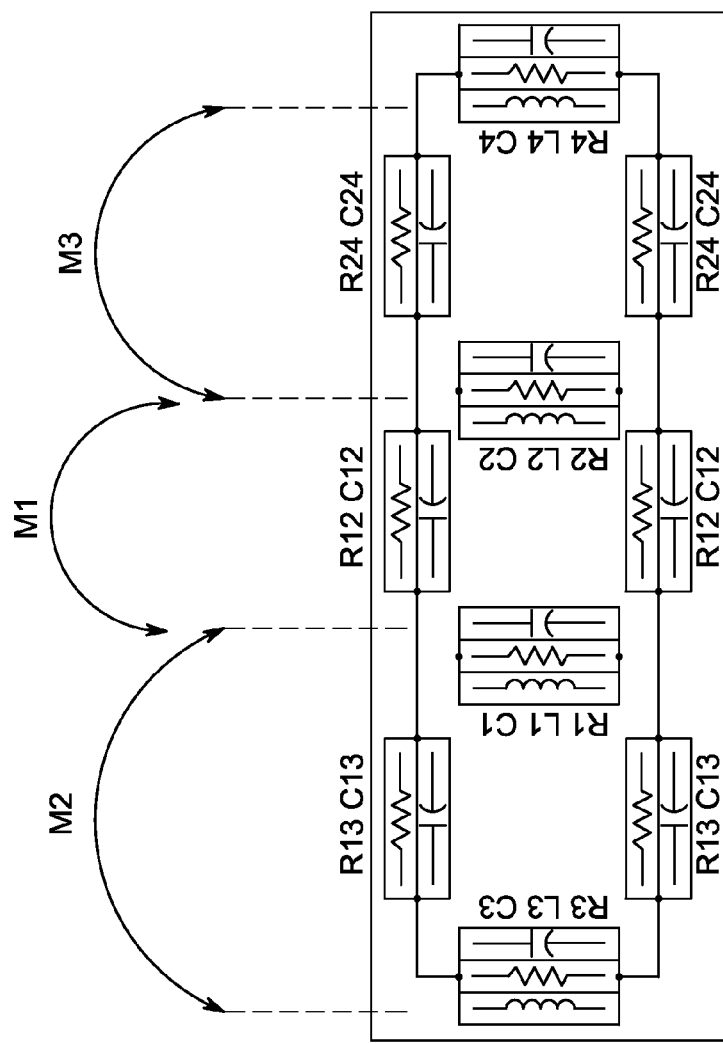
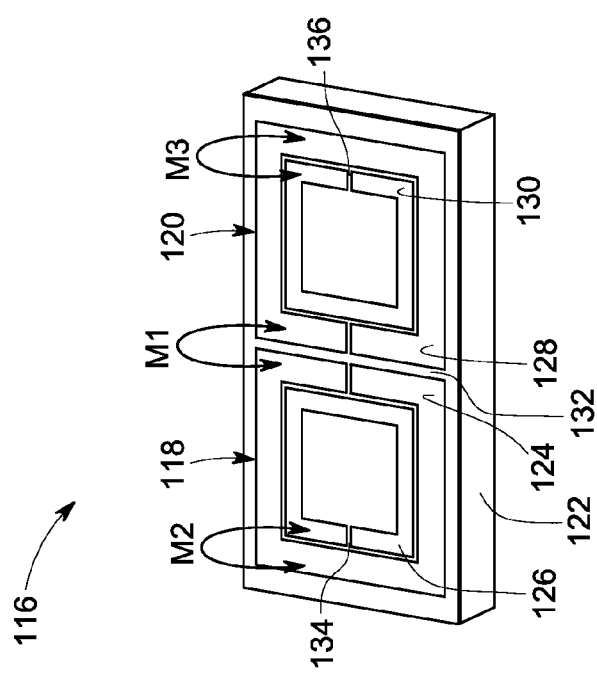
FIG. 22
FIG. 21

RESONANT SENSOR AND AN ASSOCIATED SENSING METHOD

BACKGROUND

The invention relates generally to sensing devices and more particularly to inductor-capacitor-resistor (LCR) sensing devices having enhanced selectivity and sensitivity.

Selectivity of sensors is one of the important aspects in sensor performance and applications. Typically, lack of selectivity prevents the wide use of sensors in sensing chemical and biological species in liquids and air for industrial and other applications. Two known approaches to address the problem associated with lack of selectivity include developing very selective sensing films, and combining individual diverse sensors into an array. Unfortunately, each approach suffers from its own limitations. Highly selective sensing films typically have relatively slow recovery times due to strong vapor-material interactions. Combining sensors into an array may have manufacturing challenges.

Chemical and biological detection has been accomplished using radio frequency identification (RFID) sensors. Sensor response originates from changes in dielectric properties of the sensing film deposited onto a sensor. While RFID sensors can detect individual chemical and physical changes based on changes in dielectric properties, there is a need to further improve selectivity of the RFID sensors.

BRIEF DESCRIPTION

In accordance with an exemplary embodiment of the present invention, a sensing system for selective analyte detection in presence of interferences is disclosed. The sensing system includes an inductor-capacitor-resistor (LCR) resonator sensor having a substrate, a plurality of first sensing elements mutually spaced apart and disposed on the substrate, and a sensing material film being disposed on a first sensing region of the corresponding first sensing element.

In accordance with an exemplary embodiment of the present invention, a method for measuring one or more conditions of a sample is disclosed. The method includes transmitting an electromagnetic signal from an inductor-capacitor-resistor (LCR) resonator sensor; where the LCR resonator sensor includes a substrate; a plurality of first sensing elements mutually spaced apart and disposed on the substrate; and at least one sensing film being disposed on a first sensing region of the corresponding first sensing element. The method further includes sensing the LCR resonator sensor signal via a detector.

In accordance with an exemplary embodiment of the present invention, a method for fabrication of an inductor-capacitor-resistor (LCR) resonator sensor is disclosed. The method includes applying a plurality of first sensing elements on a substrate. The method further includes applying at least one dielectric layer on the plurality of first sensing elements. The method further includes applying a plurality of second sensing elements on the at least one dielectric layer, each second sensing element being disposed corresponding to position of each first sensing element such that the at least one sensing layer is disposed between the first and second sensing elements; wherein shape of the substrate does not change during fabrication.

In accordance with an exemplary embodiment of the present invention, a method for fabrication of an inductor-capacitor-resistor (LCR) resonator sensor is disclosed. The method includes applying a plurality of first sensing elements on a substrate; and applying at least one dielectric layer on the plurality of first sensing elements. The method also includes applying a plurality of second sensing elements on the at least one dielectric layer, each second sensing element being disposed corresponding to position of each first sensing element such that the at least one dielectric layer is disposed between the plurality of first and second sensing elements. The method further includes removing a portion of dielectric layer to form a horizontal gap between the plurality of first and second sensing elements; wherein shape of the substrate does not change during fabrication.

DRAWINGS

These and other features, aspects, and advantages of the present invention will become better understood when the following detailed description is read with reference to the accompanying drawings in which like characters represent like parts throughout the drawings, wherein:

FIG. 21 is a perspective view of a dual-SRR (split ring resonator) sensor in accordance with an exemplary embodiment of the present invention;

FIG. 22 is a diagrammatical representation of a dual-SRR sensor represented as an L-C-R equivalent circuit in accordance with an exemplary embodiment of FIG. 21;

DETAILED DESCRIPTION

Figure 1:
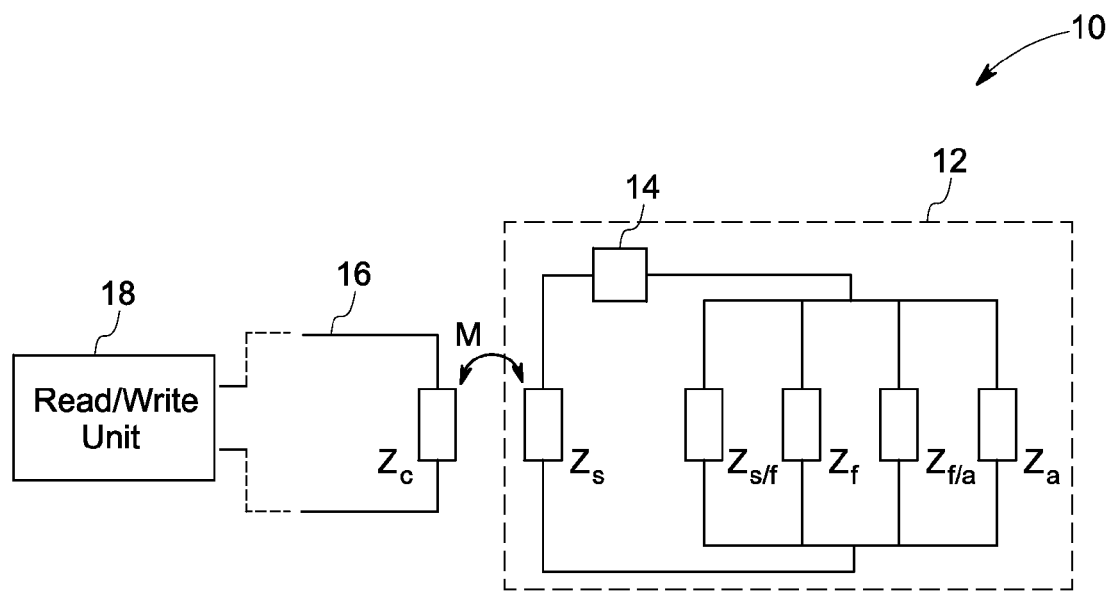
FIG. 1 is a diagrammatical representation of a sensing system, for example RFID sensing system in accordance with an exemplary embodiment of the present invention.

The embodiments of the present invention are related to a sensing system, for example an RFID sensing system for simultaneous sensing of one or more properties of a sample. As used herein, a RFID sensing system includes an inductor-capacitor-resistor (LCR) resonator sensor and an excitation element such as a pick-up coil (detector).

To more clearly and concisely describe the subject matter of the claimed invention, the following definitions are provided for specific terms, which are used in the following description and the appended claims.

The term "fluids" may include gases, vapors, liquids, and solids.

The term "analyte" includes any substance or chemical constituent that is the subject of a chemical or biological analysis. Examples of analytes include, but are not limited to, acidic or basic gases, oxidant or reducing gases, other gases, or any combination thereof. Examples of acidic or basic gases include, but are not limited to ammonia, hydrogen sulfide, methanethiol, hydrogen bromide, hydrogen chloride, hydrogen iodide, hydrogen fluoride, and so forth. Examples of oxidant or reducing gases include, but are not limited to hydrogen peroxide, chlorine dioxide, oxygen, chlorine, bromine, and so forth. Examples of other gases include, but are not limited to sulfur dioxide, arsine, hydrogen cyanide, phosgene, triacetone triperoxide, carbon dioxide, carbon monoxide, trinitrotoluene, explosives, and so forth.

The term "digital ID" includes all data stored in a memory chip of the RFID sensor. Non-limiting examples of such data are manufacturer identification, electronic pedigree data, user data, and calibration data for the sensor.

The term "monitoring process" includes, but is not limited to, measuring physical changes that occur around the sensor. For example, monitoring processes including monitoring changes in a biopharmaceutical, food or beverage manufacturing process related to changes in physical, chemical, and/or biological properties of an environment around the sensor. Monitoring processes may also include those industry processes that monitor physical changes as well as changes in a component's composition or position. Non-limiting examples include homeland security monitoring, residential home protection monitoring, environmental monitoring, clinical or bedside patient monitoring, airport security monitoring, admission ticketing, and other public events. Monitoring can be performed when the sensor signal has reached an appreciably steady state response and/or when the sensor has a dynamic response. The steady state sensor response is a response from the sensor over a determined period of time, where the response does not appreciably change over the measurement time. Thus, measurements of steady state sensor response over time produce similar values. The dynamic sensor response is a response from the sensor based upon a change in the measured environmental parameter (for example, temperature, pressure, chemical concentration, biological concentration, or the like). Thus, the dynamic sensor response significantly changes over the measurement time to produce a dynamic signature of response toward the environmental parameter or parameters measured. Non-limiting examples of the dynamic signature of the response include average response slope, average response magnitude, largest positive slope of signal response, largest negative slope of signal response, average change in signal response, maximum positive change in signal response, and maximum negative change in signal response. The produced dynamic signature of response can be used to further enhance the selectivity of the sensor in dynamic measurements of individual vapors and their mixtures. The produced dynamic signature of response can also be used to further optimize the combination of irreversible sensing material and transducer geometry to enhance the selectivity of the sensor in dynamic and steady state measurements of individual vapors and their mixtures.

The term "environmental parameters" is used to refer to measurable environmental variables within or surrounding a manufacturing or monitoring system. The measurable environmental variables include at least one of physical, chemical, and biological properties and include, but are not limited to measurement of temperature, pressure, material concentration, conductivity, dielectric property, number of dielectric, metallic, chemical, or biological particles in the proximity or in contact with the sensor, dose of ionizing radiation, and light intensity. The measurable environmental variables are also of a material in contact with the sensor such as a sensing material or a sensing film.

As used herein the term "sensing materials and sensing films" includes, but is not limited to, materials deposited onto a transducer's electronics module, such as LCR circuit components or an RFID tag, to perform the function of predictably and reproducibly affecting the impedance sensor response upon interaction with the environment. In order to prevent the material in the sensor film from leaking into the liquid environment, the sensing materials are attached to the sensor surface using standard techniques, such as covalent bonding, electrostatic bonding, and other standard techniques known to those of ordinary skill in the art.

The term "interference" includes any undesired environmental parameter that undesirably affects the accuracy and precision of measurements of the sensor. The term "interferent" refers to a fluid or an environmental parameter (that includes, but is not limited to temperature, pressure, light, or the like) that potentially may produce an interference response by the sensor.

The term "multivariate analysis" refers to a mathematical procedure that is used to analyze more than one variable from the sensor response and to provide the information about the type of at least one environmental parameter from the measured sensor spectral parameters and/or to quantitative information about the level of at least one environmental parameter from the measured sensor spectral parameters. The term "principal components analysis (PCA)" refers to a mathematical procedure that is used to reduce multidimensional data sets to lower dimensions for analysis. Principal components analysis is a part of Eigen analysis methods of statistical analysis of multivariate data and may be performed using a covariance matrix or correlation matrix. Non-limiting examples of multivariate analysis tools include canonical correlation analysis, regression analysis, nonlinear regression analysis, principal components analysis, discriminate function analysis, multidimensional scaling, linear discriminate analysis, logistic regression, or neural network analysis.

The term "multivariate sensor" is referred to herein as a single sensor capable of producing a plurality of response signals that are not substantially correlated with each other. These individual response signals from the multivariate sensor are further analyzed using one or more multivariate analysis tools to contrast the response patterns of exposures to different analytes and the different analyte concentrations. In one embodiment, multivariable or multivariate signal transduction is performed on the plurality of response signals using the one or more multivariate analysis tools to construct a multivariate sensor response pattern.

The term "spectral parameters" is used to refer to measurable variables of the sensor response. The sensor response is the impedance spectrum of the resonance sensor circuit of the LCR or RFID sensor. In addition to measuring the impedance spectrum in the form of Z-parameters, S-parameters, and other parameters, the impedance spectrum may be analyzed simultaneously using various parameters for analysis, such as the frequency of the maximum of the real part of the impedance ($F_p$), the peak magnitude of the real part of the impedance ($Z_p$), the first peak frequency of the imaginary part of the impedance ($F_1$), the second valley frequency of the imaginary part of the impedance ($F_2$), signal magnitude ($Z_1$) at the peak frequency of the imaginary part of the impedance ($F_1$), signal magnitude ($Z_2$) at the second resonant frequency of the imaginary part of the impedance ($F_2$), and zero-reactance frequency ($F_z$), frequency at which the imaginary portion of impedance is zero. Other spectral parameters may be simultaneously measured using the entire impedance spectra, for example, quality factor of resonance, phase angle, and magnitude of impedance. Collectively, "spectral parameters" calculated from the impedance spectra, may be referred to as "features" or "descriptors." The appropriate selection of features is performed from all potential features that can be calculated from spectra. Multivariable spectral parameters are described in U.S. Pat. No. 7,911,345 entitled "Methods and systems for calibration of RFID sensors," which is incorporated herein by reference.

The term "resonance impedance" or "impedance" refers to measured sensor frequency response as real and imaginary parts of impedance around the resonance of the sensor from which the sensor "spectral parameters" are extracted.

The terms "transducer" and "sensor" are used to refer to electronic devices such as RFID and LCR devices intended for sensing. "Transducer" is a device before it is coated with a sensing or protecting film or before it is calibrated for a sensing application. "Sensor" is a device typically after it is coated with a sensing or protecting film and after being calibrated for the sensing application.

As used herein the term "RFID tag" refers to an identification and reporting technology that uses electronic tags for identifying and/or tracking articles to which the RFID tag may be attached. An RFID tag typically includes at least two components where the first component is an integrated circuit (IC) memory chip for storing and processing information, and modulating and demodulating a radio frequency signal. The memory chip can also be used for other specialized functions, for example, the chip may contain a capacitor. The chip may also contain at least one input for an analog signal such as a resistance input, capacitance input, or inductance input. In the case of a chipless RFID tag, the RFID tag may not include an IC memory chip. Such an RFID tag may be useful in applications where a specific RFID tag does not need to be identified, but rather a signal merely indicating the presence of the tag that provides useful information (e.g., product security applications). The second component of the RFID tag is an antenna for receiving and transmitting the radio frequency signal.

The term "RFID sensor" is an RFID tag with an added sensing function as, for example, when an antenna of the RFID tag also performs sensing functions by changing its impedance parameters as a function of environmental changes. The accurate determinations of environmental changes using such RFID sensors are performed by analysis of resonance impedance. For example, RFID tags may be converted into RFID sensors by coating the RFID tag with a sensing film. By coating the RFID tag with a sensing film, the electrical response of the film is translated into simultaneous changes to the impedance response, resonance peak position, peak width, peak height and peak symmetry of the impedance response of the sensor antenna, magnitude of the real part of the impedance, resonant frequency of the imaginary part of the impedance, anti-resonant frequency of the imaginary part of the impedance, zero-reactance frequency, phase angle, and magnitude of impedance, and others as described in the definition of the term sensor "spectral parameters." The "RFID sensor" may have an integrated circuit (IC) memory chip attached to the antenna or may have no IC memory chip. An RFID sensor without an IC memory chip is an LCR sensor. An LCR sensor includes components, such as at least one inductor (L), at least one capacitor (C), and at least one resistor (R) to form an LCR circuit.

The term "writer/reader" includes, but is not limited to, a combination of devices to write and read data into the memory of the memory chip and to read impedance of the antenna. The term "writer/reader" may also be referred to as an "interrogator."

In accordance with embodiments disclosed herein, an LCR or an RFID sensor for sensing vapors, vapor mixtures, and biological species is described. As previously described, the RFID sensor includes an RFID tag coated with an irreversible sensing material. In one embodiment, a passive RFID tag may be employed. As will be appreciated, an RFID tag may include an IC memory chip, which is connected to an antenna coil for communication with a writer/reader. The IC memory chip can be read by illuminating the tag by a radio frequency (RF) and/or microwave carrier signal sent by the writer/reader. When the RF and/or microwave field passes through the antenna coil, an AC voltage is generated across the coil. The voltage is rectified in the microchip to result in a DC voltage for the microchip operation. The IC memory chip becomes functional when the DC voltage reaches a predetermined level. By detecting the RF and/or microwave signal backscattered from the microchip, the information stored in the microchip can be fully identified. The distance between the RFID tag/sensor and the writer/reader is governed by the design parameters that include operating frequency, RF and/or microwave power level, the receiving sensitivity of the reader/writer, antenna dimensions, data rate, communication protocol, and microchip power requirements. The distance between the "RFID sensor" without an IC memory chip (chipless RFID sensor or LCR sensor or LCR transducer) and the sensor reader is governed by the design parameters that include operating frequency, RF or microwave power level, the receiving sensitivity of the sensor reader, and antenna dimensions.

Sensor response originates from changes in dielectric and dimensional properties of a sensing film deposited onto a LCR resonator sensor. A change in dielectric property of the sensing film is measured by measuring the resonance response of the LCR sensor. The LCR sensor may be used for sensing one or more properties of a sample. Properties may include a physical condition, a biological condition, or a chemical condition and may include a quantitative response for a desired parameter. For example, the sensor may be employed to monitor magnitude of an environmental parameter of interest such as, but not limited to, conductivity measurement, pH level, temperature, blood relevant measurement, ionic measurement, non-ionic measurement, non-conductivity measurement, electromagnetic radiation level measurement, pressure, vapor concentration, biological material concentration, and other types of measurements that may be taken from a typical sample (solution or gas or solid). The selectivity of the LCR resonator sensor is provided by at least three orthogonal responses related to the variation of the sensor inductance, capacitance, and resistance. These orthogonal responses are provided by the combination of the sensor geometry, data acquisition, sensing material of the sensing film, and multivariate data analysis techniques. It should be noted herein that in accordance with the embodiments of the present invention, the LCR resonator sensor may be referred to as "a multivariate sensor".

The multivariate resonant sensor generates a plurality of orthogonal responses defined as the number of orthogonal axes generated after the multivariate analysis that include the analyte-relevant information.

In certain embodiments, the sample may include a container such as a disposable container, a bioreactor, a stainless steel container, a plastic container, a polymeric material container, or a pre-sterilized polymeric material container. Further, the container may be of different size and shape, for example, a micro fluidic channel, a Petri dish, a glove box, a hood, or a plastic bag. The sample can also be an indoor enclosure or an outdoor monitoring station. In certain embodiments, the container is a disposable bioprocess component. Non-limiting examples of the bioprocess component include a disposable storage bag, a disposable container, a product transfer line, a filter, a connector, a valve, a pump, a bioreactor, a separation column, a mixer, or a centrifugation system. In one embodiment, the disposable container or bag may be made of plastic. The disposable container may include ports for inserting the LCR resonant sensor and the pick-up coil. In one embodiment, the sensor and the pick-up coil may be inserted in the container using the same port. In other embodiment, the sensor and the pick-up coil may be inserted in the container using separate ports. For example, the sensor may be used in conjunction with disposable bioprocess components to monitor the parameters inside the components during or after the operation. In certain embodiments, the LCR sensor functions by generating a sensor output that relies on a coupling between the LCR sensor and a corresponding pick-up coil.

Now referring to FIG. 1, a sensing system, for example a radio frequency identification (RFID) sensing system 10 in accordance with an exemplary embodiment is disclosed. In the illustrated embodiment, an equivalent sensor circuit of the system 10 is shown. The sensing system 10 includes an LCR sensor 12 with an IC memory chip 14, a pick-up coil (detector) 16. The IC memory chip 14 is used for storing information and may be activated by a radio frequency signal transmitted from a read/write unit 18. The sensor 12 receives and transmits radio frequency signals. The pick-up coil 16 is disposed in operative proximity of the sensor 12 so as to pick up signals transmitted by the sensor 12. In one embodiment, the sensor 12 and the pick-up coil 16 may be coupled via an inductive coupling. In a preferred embodiment, the sensor 12 and the pick-up coil 16 may be adapted to communicate wirelessly. In certain embodiments, an IC memory chip is not required and an LCR sensor 12 can operate without the IC memory chip.

The memory chip 14 is read by the read/write unit 18 by illuminating the sensor 12 tuned by a combination of a sensor inductance (L), a sensor capacitance (C), and a sensor resistance (R). The combination of the inductance, the capacitance, and the resistance is termed an "LCR resonant circuit". When a radio frequency field passes through a sensor coil (not shown in FIG. 1), an AC voltage is generated across the sensor coil. This voltage is rectified in the memory chip 14 to result in a DC voltage for the chip operation. The chip 14 becomes functional when the DC voltage reaches a predetermined level needed to activate and operate the memory chip 14. By detecting the radio frequency signal backscattered from the memory chip 14, the information stored in the memory chip 14 can be identified.

To activate the memory chip 14, the read/write unit 18 sends a radio frequency signal that is captured by the sensor coil of the sensor 12, generating an AC voltage across the sensor coil. An on-chip rectifier (not shown) further converts the AC voltage into a DC voltage that activates the memory chip 14. The activated chip 14 is capable of sending stored information back to the read/write unit 18 and is capable of receiving new information to be stored into the memory. The read/write unit 18 uses command pulses to communicate with the chip 14 for reading and writing data.

For selective analyte quantitation using the LCR sensor 12, impedance spectra of the sensor are measured. "Analyte" refers to the substance or condition being analyzed. In the illustrated embodiment, the sensor circuit of the sensor 12 is represented by impedance ($Z_s$) of an electrode structure, impedance ($Z_{s/f}$) of a sensing film, impedance ($Z_f$) of an interface between the electrode structure and the sensing film, impedance ($Z_{f/a}$) of an interface between the sensing film and an analyzed fluid, impedance ($Z_a$) of the analyzed fluid. In the illustrated embodiment, the impedances are shown in parallel. In certain other embodiments, the impedances may be in series. The sensor 12 is interrogated via the pick-up coil 16 having an impedance ($Z_c$).

Figure 2:
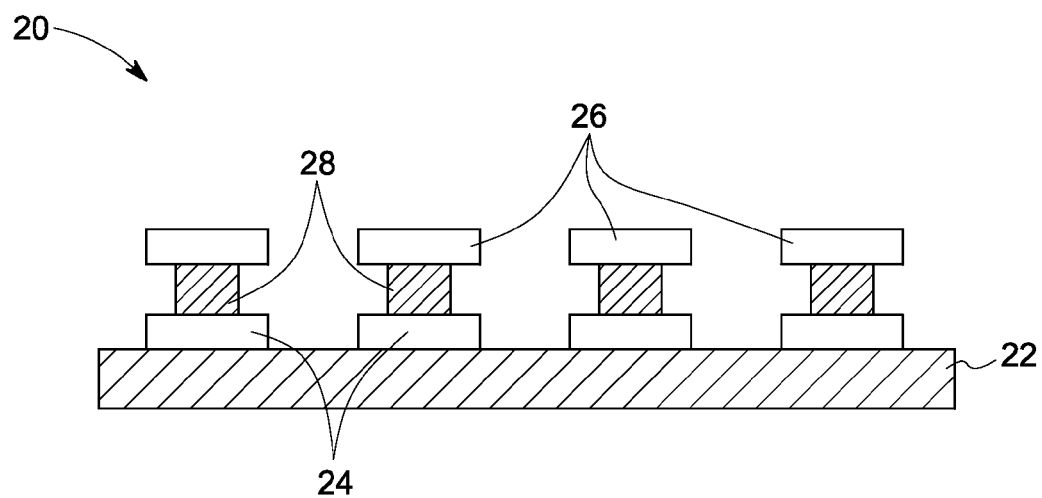
FIG. 2 is a sectional view of an electrode structure of an LCR sensor in accordance with an exemplary embodiment of the present invention.

Referring to FIG. 2, an electrode structure 20 of the LCR sensor in accordance with an exemplary embodiment of the present invention is disclosed. In the illustrated embodiment, the electrode structure 20 includes a substrate 22, a plurality of first sensing elements 24 mutually spaced apart and disposed on the substrate 22. The electrode structure 20 further includes a plurality of second sensing elements 26; each second sensing element 26 is disposed overlapping the corresponding first sensing element 24. An isolator 28 (may also be referred to as a "dielectric layer") is disposed between the corresponding first and second sensing elements 24, 26. The isolator 28 may be used to prevent electrical shortening and loss of the sensor resonance. In some embodiments, the LCR sensor is a multivariable LCR sensor. In certain embodiments, the first sensing element 24 is non-galvanically coupled to second sensing element 26.

Figure 3:
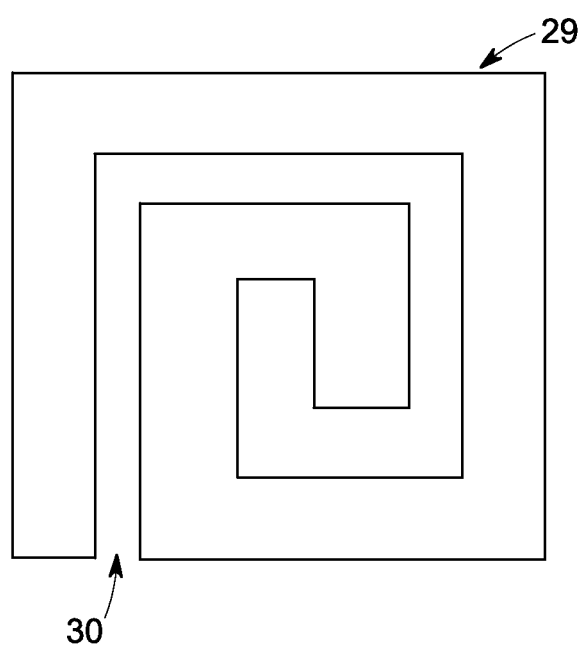
FIG. 3 is a top view of the electrode structure in accordance with an embodiment of FIG. 2.

Referring to FIG. 3, a top view of the electrode structure 20 (shown in FIG. 2) is illustrated. It should be noted herein that the plurality of first and second sensing elements 24, 26 (shown in FIG. 2) together form a sensing coil structure 29. Such a sensing coil structure 29 may be fabricated using techniques not limited to a complementary metal-oxide-semiconductor (CMOS) fabrication process, inkjet printing, screen printing, laser cutting, selective etching, or the like. In some embodiments, groups of such sensing elements 24, 26 form an array of such coil structures 29. It should be noted herein that the number of sensing elements, their orientation, and geometry may be varied depending upon the application. In some embodiments, groups of such sensing elements 24, 26 form an array of structures that are not coils but other types of LCR resonators. Non-limiting examples of such LCR resonators operating at different frequencies are split ring resonators with a single or multiple cuts, dual-split ring resonators, closed rings, slab-pairs, cross-shaped structures, coupled strips, posts, wires, and their combinations.

Fabrication of the sensing elements to form a coil structure 29 with a dielectric gap 30, for example, provides the ability to obtain inductance of the sensing elements. Such an inductance directly contributes to the LCR sensor performance. Also, fabrication of the sensing elements as interdigital electrodes on top of each other and separated with a dielectric gap provides the ability to obtain large area for interactions with environment around the sensing elements. Furthermore, fabrication of the sensing elements as other types of LCR structures with nonlimiting examples of geometries as described above with one on top of each other and separated with a dielectric gap provides the ability to obtain large area for interactions with environment around the sensing elements.

Figure 4:
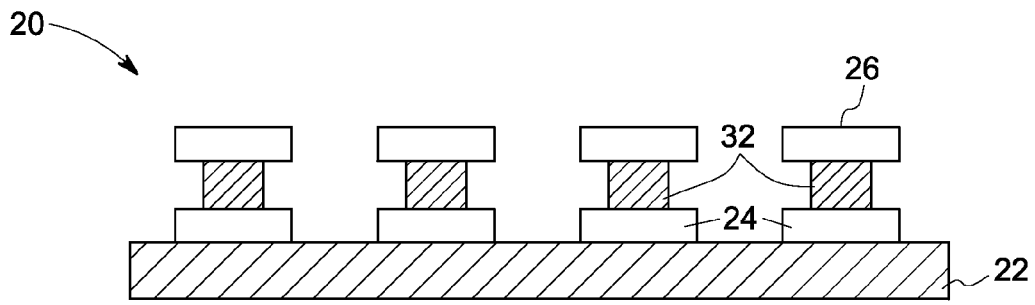
FIG. 4 is a sectional view of an electrode structure in accordance with an exemplary embodiment of the present invention.

Referring to FIG. 4, the electrode structure 20 in accordance with an exemplary embodiment of the present invention is disclosed. In the illustrated embodiment, a dielectric gap material 32 between the first and second sensing elements 24, 26 may serve as a "sensing layer". The height and a dielectric constant of the dielectric gap material 32 may vary depending upon interactions with the analytes. The height of the dielectric gap material 32 may vary due to swelling of the dielectric gap material 32 because of the sorption uptake of an analyte. The dielectric constant of the dielectric gap material 32 may also vary because of the sorption uptake of an analyte.

In one embodiment, the electrode structure 20 may be fabricated by first applying the plurality of first sensing elements 24 to the substrate 22 having a predetermined shape. The dielectric layer 32 is then applied to the plurality of first sensing elements 24. The plurality of second sensing elements 26 is then applied corresponding to the positions of the plurality of first sensing elements 24, where the dielectric layer 32 is disposed separating the plurality of first and second sensing elements 24, 26. The shape of the substrate 22 does not change during the fabrication process. In some embodiments, the at least one dielectric layer 32 has a thickness in a range of one to five thousand nanometers.

In another embodiment, the electrode structure 20 may be fabricated by first applying the plurality of first sensing elements 24 to the substrate 22 having a predetermined shape. The dielectric layer 32 is then applied to the plurality of first sensing elements 24. The plurality of second sensing elements 26 is then applied corresponding to the positions of the plurality of first sensing elements 24, where the dielectric layer 32 is disposed separating the plurality of first and second sensing elements 24, 26. A portion of the dielectric layer 32 is removed to form a horizontal gap between the first and second sensing elements 24, 26. The shape of the substrate 22 does not change during the fabrication process. In some embodiments, the at least one dielectric layer 32 has a thickness in a range of one to five thousand nanometers.

Figure 5:
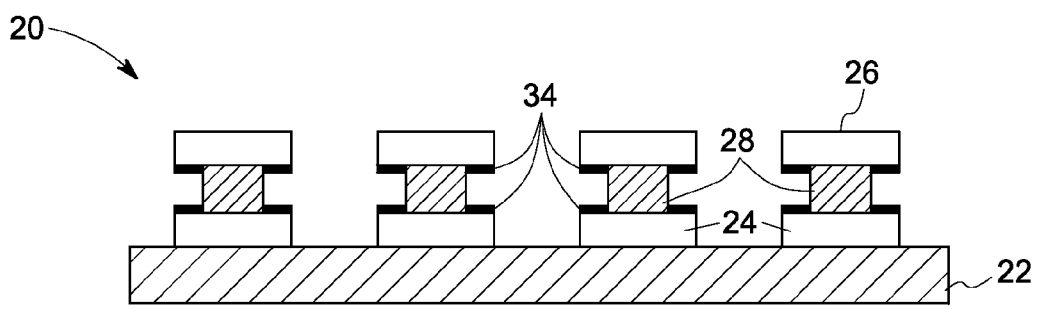
FIG. 5 is a sectional view of an electrode structure in accordance with an exemplary embodiment of the present invention.

Referring to FIG. 5, the electrode structure 20 in accordance with an exemplary embodiment of the present invention is disclosed. In the illustrated embodiment, a gap between the first and second sensing elements 24, 26 may be functionalized by applying a sensing film 34. The same sensing film 34 may be provided to both the first and second sensing elements 24, 26.

The sensing film 34 performs the function of predictably and reproducibly affecting the sensor response upon interaction with a sample. The sensing film material may include a polymeric, organic, inorganic, biological, composite, or a nano composite film that changes property depending on the environment that material is placed in. Additional examples of sensing materials include ionic liquids with organic and inorganic ions, semiconducting nanocrystals, nanotubes, and nano fibers. Additional examples of sensing materials can be in the form of organic molecules, biological molecules, and inorganic molecules. The sensing material can be also in the form of biological organisms such as cells, bacteria, and others known in the art to respond to the environmental changes of the environment.

Examples of properties of a sensing material that are predictably changing upon exposure to the environment include, but are not limited to, changes in capacitance, changes in resistance, changes in thickness, changes in viscoelasticity, or a combination thereof.

Figure 6:
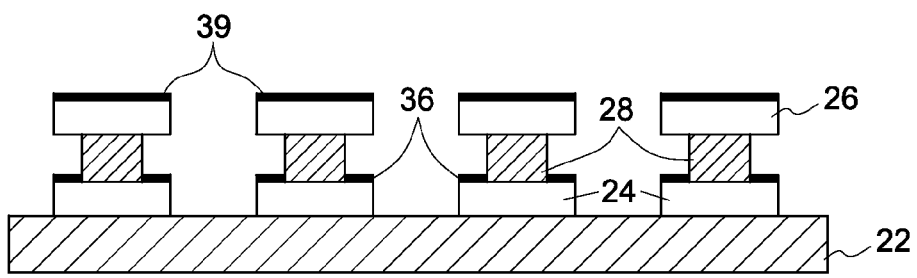
FIG. 6 is a sectional view of an electrode structure in accordance with an exemplary embodiment of the present invention.

Referring to FIG. 6, the electrode structure 20 in accordance with an exemplary embodiment of the present invention is disclosed. In the illustrated embodiment, the first and second sensing elements 24, 26 may be functionalized by applying different sensing films 36, 38 to the first and second sensing elements 24, 26. In particular, each sensing film among the one set of sensing films 26, is disposed on a first sensing region 37 of the corresponding first sensing element 24. Each sensing film among the other set of sensing films 38, is disposed on a second sensing region 39 of the corresponding second sensing element 26. The isolator 28 is disposed between the corresponding first and second sensing elements 24, 26.

In the LCR sensor, sensing response is provided from analyte-dependent change in circuit capacitance, analyte-dependent change in circuit resistance, analyte-dependent change in circuit inductance, or a combination of the three. The combination of changes in the inductance, capacitance and resistance is measured by measuring frequency response spectrum of the LCR resonant sensing circuit. The sensing films 36, 38 are selected for the proper chemical or biological recognition based on the analyte and sensing material properties. The analyte-induced changes in the sensing films 26, 32 affect the impedance of the sensor circuit through the changes in circuit resistance, circuit inductance, and circuit capacitance.

The gap between the sensing elements 24, 26 is controlled by the fabrication process and the intended application of the resulting resonant sensor. The gap between the sensing elements ranging from about 1 nanometer to about 1000 nanometers provides the ability for detection of biological molecules and structures with non-limiting examples that include nucleic acids, proteins, and viruses. The gap between sensing elements ranging from about 1 micrometer to about 1000 micrometers provides the ability for detection of biological molecules and structures with non-limiting examples that include nucleic acids, proteins, viruses, spores, bacteria.

The gap between sensing elements ranging from about 1 nanometer to about 1000 micrometers provides the ability to detect different gaseous analytes when at least one sensing film is positioned within the gap. The gap between sensing elements ranging from about 1 nanometer to about 100 millimeters provides the ability to detect at least one fluid when the fluid is positioned within the gap. The cross-sectional shapes of the sensing elements and the respective gaps between the sensing elements are governed by the intended application of the resonant sensor and the spectral range of performance of the resonant sensor. The cross-sectional shapes of the sensing elements and the respective gaps between the sensing elements can be symmetrical or non-symmetrical, as guided by the design rules of the respective LCR resonators for different frequency ranges.

Figure 7:
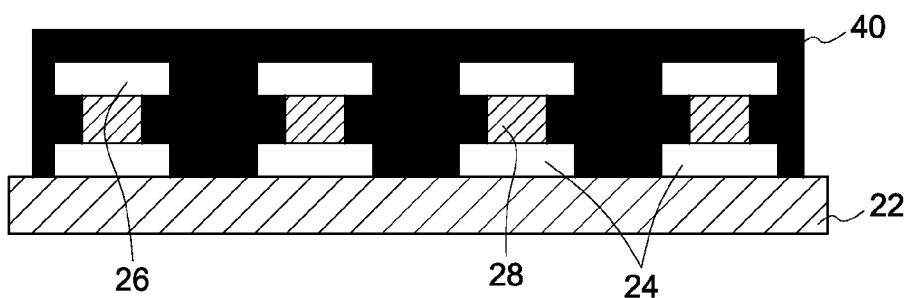
FIG. 7 is a sectional view of an electrode structure in accordance with an exemplary embodiment of the present invention.

Referring to FIG. 7, the electrode structure 20 in accordance with an exemplary embodiment of the present invention is disclosed. In the illustrated embodiment, the first and second sensing elements 24, 26 may be substantially covered with the same sensing film 40.

In accordance with the embodiments discussed herein, fabrication of gaps between sensing elements include a 3-D micro-gap, nano-gap resonator sensors for physical, chemical, and biological sensing. These 3-D micro-gaps, and nano-gaps are the working gaps responsible for the sensor response. These gaps are formed parallel to the substrate 22 of the sensor during the fabrication of the sensor. These gaps are formed parallel to the substrate 22 of the sensor during the fabrication of the sensor without a step of folding the substrate when a gap between the sensing elements is formed after substrate folding.

The 3-D micro-gap or nano-gap in the resonator sensor facilitates high sensitivity measurements, and also enables wired or wireless readout. The 3-D micro-gap or nano-gap is related to the operational frequency of the antenna of the resonant sensor where the operational frequency range from hundreds of kHz to MHz, GHz, THz, IR, near-IR, visible, and UV spectral ranges.

In conventional resonant sensors, a sensing gap is formed vertically between the sensing elements. In accordance with embodiments of the present invention employing a 3-D approach, gap is formed horizontally between the sensing elements. Such an exemplary approach provides the ability for a controlled formation of nano-gaps with high aspect ratio. Further, the horizontal gap between the sensing elements provides a relatively larger sensing volume as compared to the vertical gap in conventional resonant sensors because of the limitation of the maximum height of sensing elements that can be fabricated with the vertical gaps.

Figure 8:
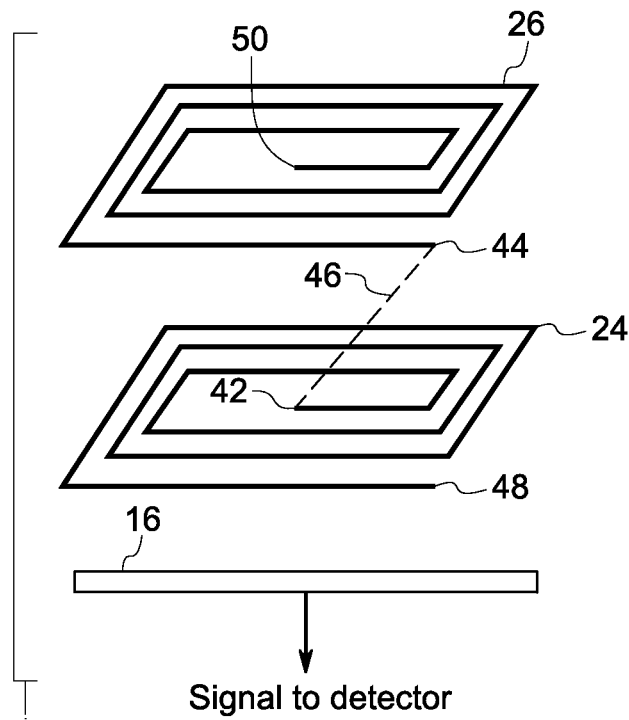
FIG. 8 is a diagrammatical representation of a first sensing element and the second sensing element of an electrode structure in accordance with an exemplary embodiment of the present invention.

Referring to FIG. 8, a diagrammatical representation of the first sensing element 24 and the second sensing element 26 is shown in accordance with an exemplary embodiment of the present invention. The second sensing element 26 is spaced apart and disposed overlapping the first sensing element 24. The first and second sensing elements 24, 26 are disposed proximate to the pick-up coil 16.

In the illustrated embodiment, a first end 42 of the first sensing element 24 is coupled to one end 44 of the second sensing element 26 via a connector 46. In another embodiment, a second end 48 of the first sensing element 24 is coupled to another end 50 of the second sensing element 26. In yet another embodiment, the first end 42 of the first sensing element 24 is coupled to the other end 50 of the second sensing element 30. In yet another embodiment, the second end 48 of the first sensing element 24 is coupled to one end 44 of the second sensing element 26. In the illustrated embodiment, the first and second sensing elements 24, 26 are wireless sensing elements. The term "wireless" indicates that there is no electrical (galvanic) contact between the resonant sensor and the sensor reader. Instead, the connection between the resonant sensor and the sensor reader is performed either through inductive coupling, capacitive coupling, or optical coupling.

Figure 9:
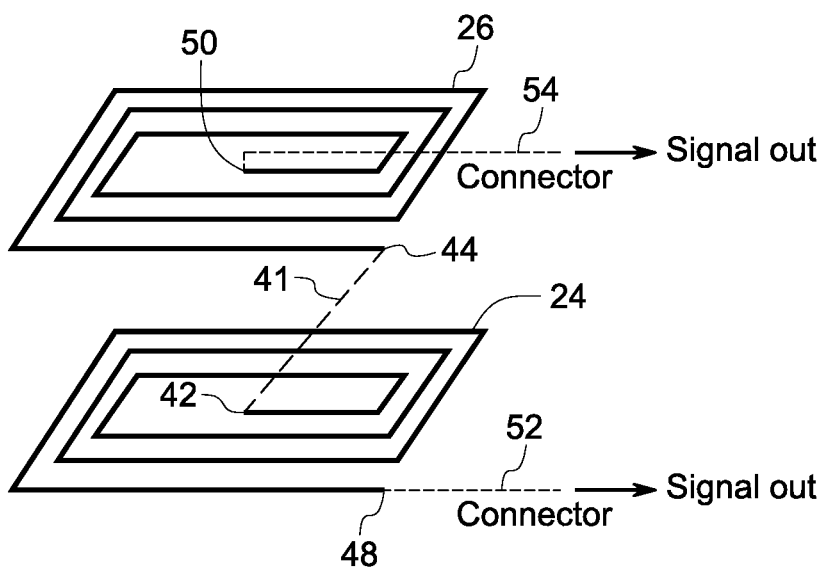
FIG. 9 is a diagrammatical representation of a first sensing element and the second sensing element of an electrode structure in accordance with an exemplary embodiment of the present invention.

Referring to FIG. 9, a diagrammatical representation of the first sensing element 24 and the second sensing element 26 is shown in accordance with an exemplary embodiment of the present invention. The second sensing element 26 is spaced apart and disposed overlapping the first sensing element 24. In the illustrated embodiment, the first and second sensing elements 24, 30 have connectors 52, 54 respectively for transmitting sensor outputs. In other words, the first and second sensing elements 24, 26 are wired sensing elements.

Figure 10:
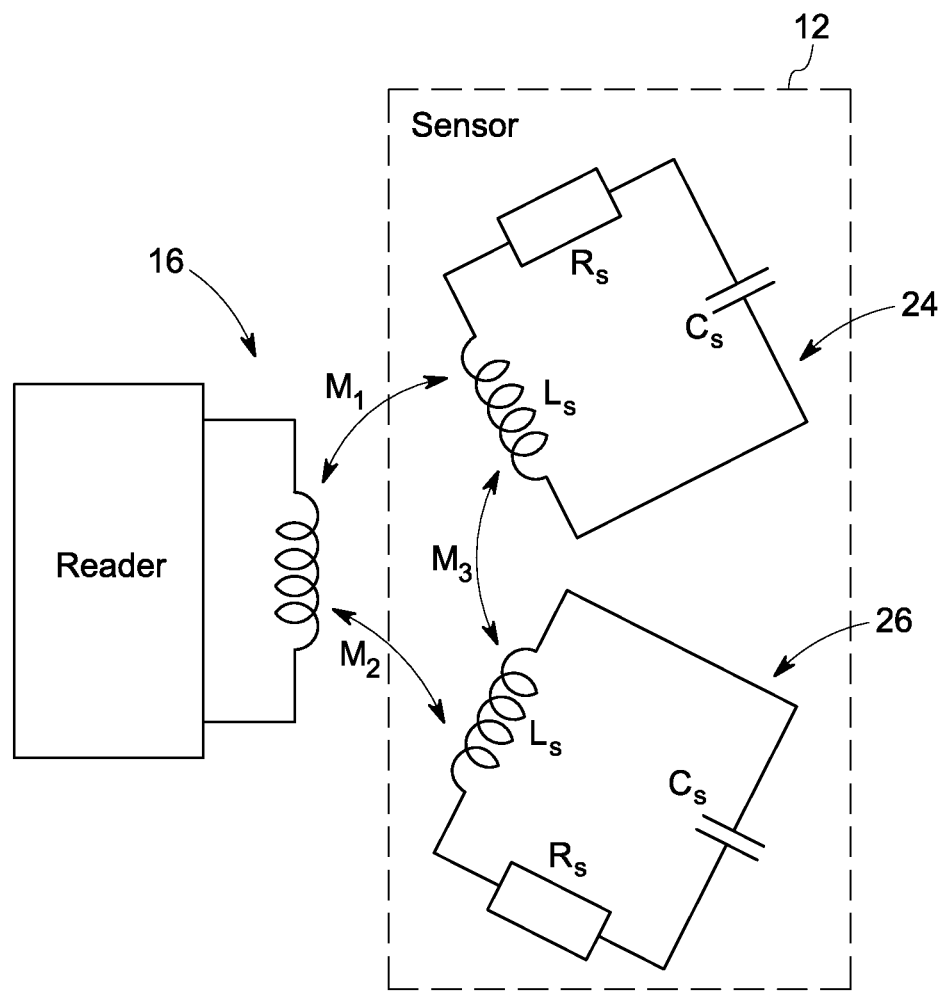
FIG. 10 is a diagrammatical representation of an LCR sensor disposed in proximity to the pick-up coil in accordance with an exemplary embodiment of the present invention.

Referring to FIG. 10, a diagrammatical representation of the LCR sensor 12 disposed in proximity to the pick-up coil 16 is disclosed. The sensor 12 has two sensing elements 24, 26 that are inductively coupled with each other and are inductively coupled to the pick-up coil 16. Inductance between the first sensing element 24 and the pick-up coil 16 is represented by "$M_1$", inductance between the second sensing element 26 and the pick-up coil 16 is represented by "$M_2$", and inductance between the first and second sensing elements 24, 26 is represented by "$M_3$". Each of the sensing elements is tuned by a combination of a sensor inductance (L), a sensor capacitance (C), and a sensor resistance (R).

It should be noted herein that the feature of using at least two sensing elements 24, 26 in the resonant sensor is to introduce an orthogonal response which is the number of orthogonal axes after the multivariate analysis that contains the analyte-relevant information and correlates with the amount of detected analyte.

An individual LCR sensor typically produces a capacitive and resistive response. A change in the position between the pickup coil and the sensor also affects the inductance response but this inductance response is unrelated to analyte concentration but rather related to the pick-up coil positioning. In accordance with the embodiments of the present invention, the fabrication of a resonant sensor with two or more sensing elements on a single substrate provides the ability to modulate inductance of the resulting sensor. The inductance is modulated when sensing elements change their position relative to each other as a function of analyte type and concentration. In one embodiment, change in position of the sensing elements is induced by swelling of the micro-gap or nano-gap (see FIG. 4). In another embodiment, the change in position of the sensing elements is induced by swelling of the sensing film (see FIG. 4) that changes the geometry of the sensing elements.

Figure 11:
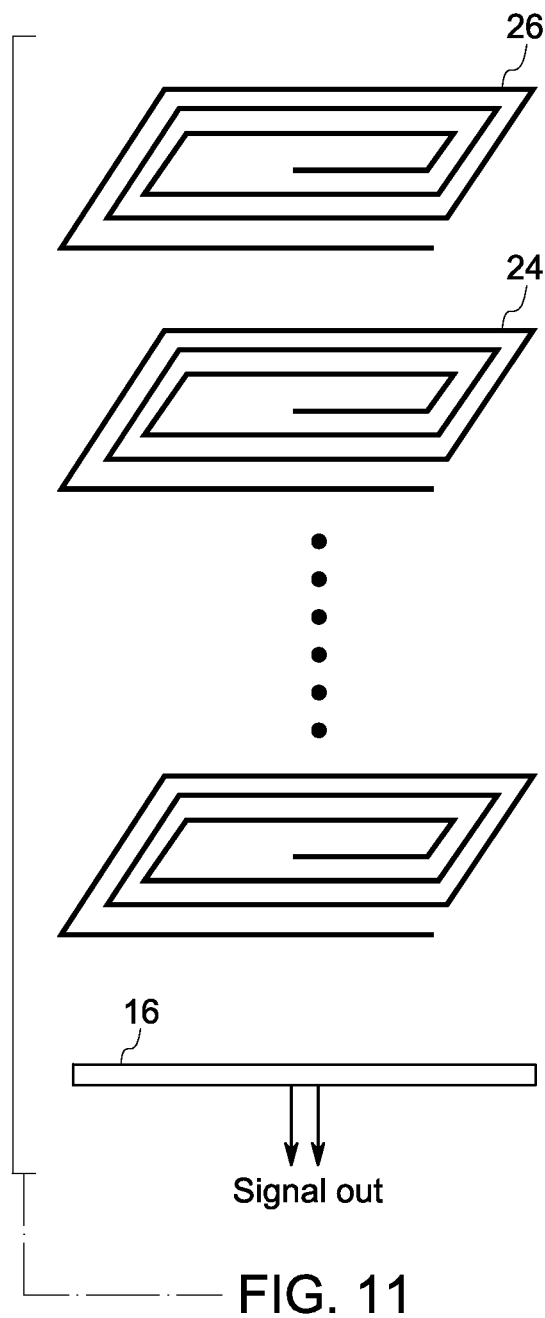
FIG. 11 is a diagrammatical representation of a plurality of sensing elements in accordance with an exemplary embodiment of the present invention.

Referring to FIG. 11, a diagrammatical representation of a plurality of sensing elements is shown in accordance with an embodiment of the present invention. The plurality of sensing elements are spaced apart and disposed overlapping each other. A sensor signal is received wirelessly using the pick-up coil 16.

The LCR resonator sensor may be operated in the radio-frequency range, microwave range, and optical range depending on the operation frequency range of the sensor. In these operation ranges, wireless excitation of the LCR resonator sensor and signal collection from the LCR resonator sensor may be performed using different methods. In one embodiment, for a radio-frequency range operation of the sensor, non-limiting examples include wireless excitation and signal collection via a pick-up coil. In another embodiment, for a microwave range operation of the sensor, non-limiting examples include wireless excitation and signal collection via a monopole antenna and a horn antenna. In yet another embodiment, for an optical range operation of the sensor, non-limiting examples include wireless excitation and signal collection via a halogen lamp and a spectrometer.

Figure 12:
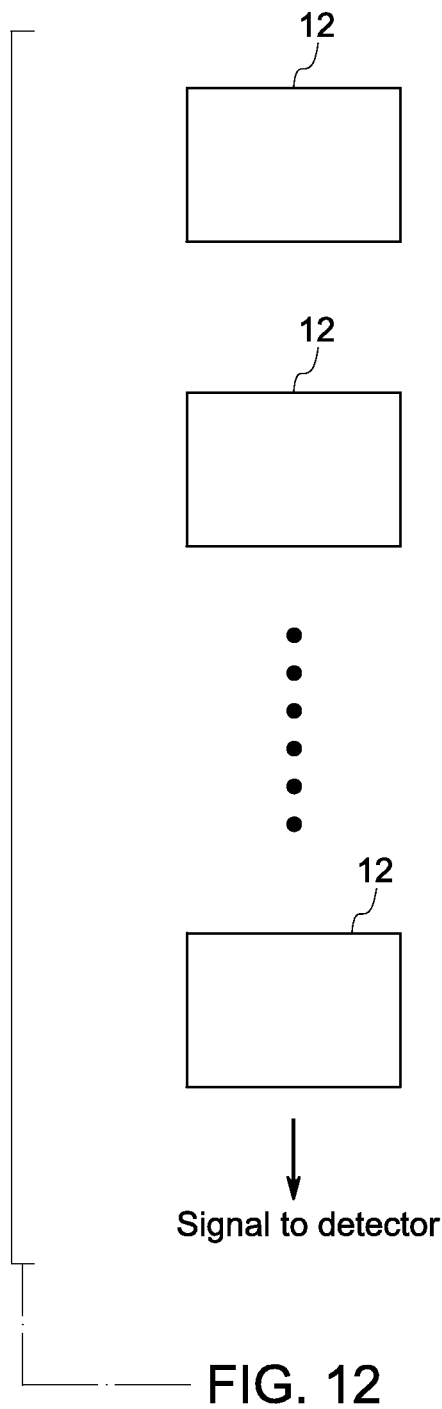
FIG. 12 is a diagrammatical representation of a plurality of LCR sensors in accordance with an exemplary embodiment of the present invention.

Referring to FIG. 12, a diagrammatical representation of a plurality of LCR sensors 12 are shown in accordance with an embodiment of the present invention. In one embodiment, "n" number of LCR sensors 12 are disposed proximate to the pick-up coil. In certain embodiments, "n" number of corresponding pick-up coils may be used. The number of pick-up coils and LCR sensors 12 may vary depending on the application. The sensor excitation response may be detected and analyzed via a network analyzer or other measurement system. In some embodiments, instead of a pick-up coil, other techniques may be used for receiving signals based on frequency range of measurements.

Figure 13:
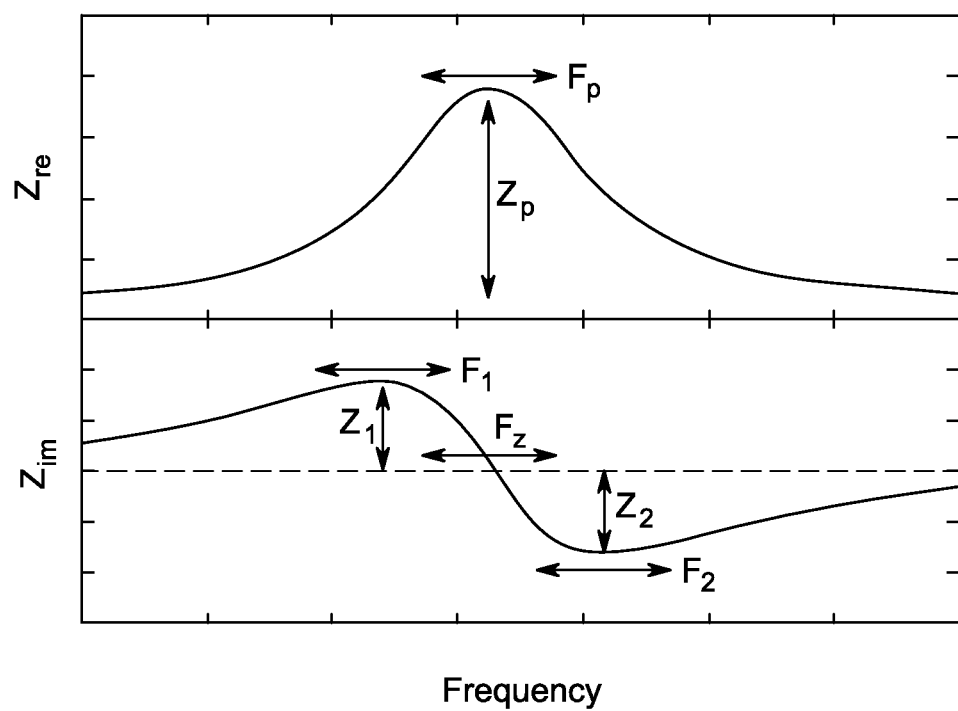
FIG. 13 is graphical representation of an impedance spectrum of an LCR sensor used for measuring one or more properties of an analyte, in accordance with an exemplary embodiment of the present invention.

Referring to FIG. 13, an impedance spectrum of the LCR sensor for measuring one or more properties of an analyte is illustrated in accordance with an embodiment of the present invention. X-axis is represented by "frequency" of the spectrum and Y-axis is represented by "impedance" (Z) of the spectrum. The spectrum includes a real part ($Z_{re}$) of the impedance spectrum, an imaginary part ($Z_{im}$) of the impedance spectrum, frequency of the maximum of the real part of the impedance ($F_p$), peak magnitude of the real part of the impedance ($Z_p$), peak frequency ($F_1$) and magnitude ($Z_1$) of the imaginary part of the impedance, resonant frequency ($F_2$) and magnitude ($Z_2$) of the imaginary part of the impedance, and frequency ($F_z$) at which the imaginary portion of impedance is zero.

Additional parameters that can be extracted from a response of the LCR sensor circuit may include quality factor of resonance, phase angle, or the like. Use of multivariate analysis reduces the dimensionality of the multivariable LCR sensor response to a single data point in multidimensional space for selective quantitation of different parameters of an analyte. Examples of multivariate analysis include canonical correlation analysis, regression analysis, nonlinear regression analysis, principal components analysis, discriminate function analysis, multidimensional scaling, linear discriminate analysis, logistic regression, and/or neural network analysis. Quantitation of analytes is performed using the exemplary LCR sensor by applying multivariate analysis of the full impedance spectrum. In certain embodiments, other spectral parameters, related to the impedance spectrum such as S-parameters (scattering parameters) and Y-parameters (admittance parameters) may be measured.

Figure 14:
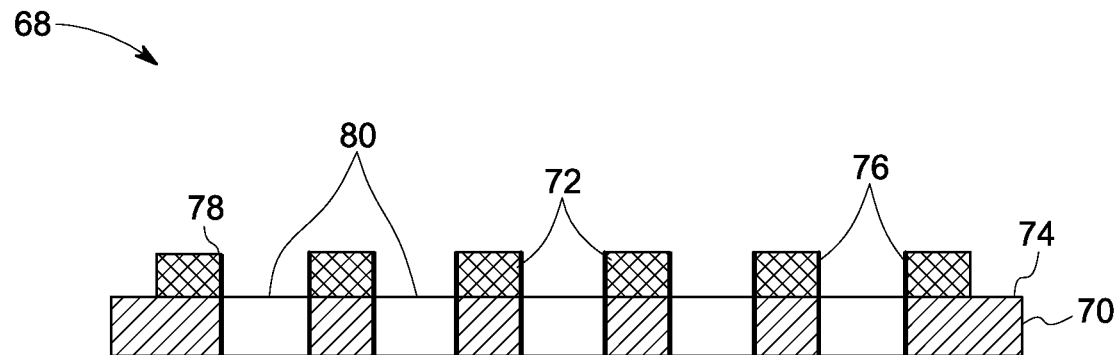
FIG. 14 is a sectional view of an electrode structure of an LCR sensor in accordance with an exemplary embodiment of the present invention.

Referring to FIG. 14, an electrode structure 68 of an LCR sensor in accordance with an exemplary embodiment of the present invention is disclosed. In the illustrated embodiment, the electrode structure 68 includes a substrate 70, a plurality of first sensing elements 72 mutually spaced apart and disposed on a first surface 74 of the substrate 70, one set of sensing films 76, each sensing film among the one set of sensing films 76, being disposed on a first sensing region 78 of the corresponding first sensing element 72. In the illustrated embodiment, the first sensing region 78 is a vertical region of the first sensing element 72. The substrate 70 further includes a plurality of holes 80 formed in the substrate 70; the holes 80 being disposed between the plurality of first sensing elements 72. The holes 80 facilitate flow of the sample medium through the substrate 70. Non-limiting examples of positioning of sensing films 76 include vertical regions of the first sensing elements 72 and/or on the vertical regions on holes 80 in the substrate 70.

The electrode structure 68 in accordance with this embodiment provides the ability for measurements of biological samples in a flow-through configuration that significantly reduces the time needed to achieve sensor response because of the mass-transport limitation.

In the illustrated embodiment, an electrical field distribution between the sensing elements 72 is substantially uniform in the plane of electrode structure 68 i.e. the electric field distribution between the plurality of first sensing elements 72 is substantially uniform along a plane of the plurality of first sensing elements 72 and the holes 80. Having the sensing holes 80 between the sensing elements 72 for the flow-through of biological molecules and particles (such as viruses, bacteria, spores, etc.) provides the advantage of reliable detection of these biological moieties in any region of the sensing holes 80. In some embodiments, the sensing holes 80 may further include nano-holes or micro-holes for the flow-through of the sample. In certain embodiments, the interior of the sensing holes 80 may be functionalized by a receptor film layer to provide selective detection. The plurality of nano-holes or micro-holes in the sensing holes may be also functionalized using a receptor film layer to provide selective detection. The plurality of nano-holes or micro-holes in the sensing holes 80 increases the surface area for interaction of the receptor film layer with an analyte passing through the sensing holes. The flow-through configuration of the illustrated embodiment, enables reductions in assay time and sample volumes, enhancing the utility of sensors.

Figure 15:
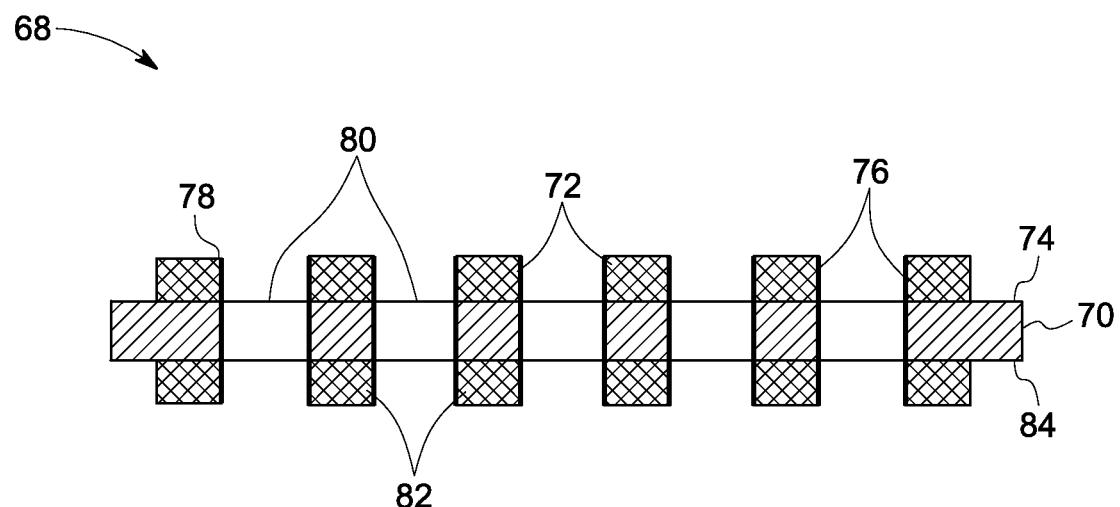
FIG. 15 is a sectional view of an electrode structure of an LCR sensor in accordance with an exemplary embodiment of the present invention.

Referring to FIG. 15, an electrode structure 68 of an LCR sensor in accordance with an exemplary embodiment of the present invention is disclosed. The electrode structure 68 is similar to the embodiment of FIG. 14. Additionally, the electrode structure 68 further includes a plurality of second sensing elements 82 disposed on a second surface 84 opposite to the first surface 74 of the substrate 70. The plurality of holes 80 in the substrate 70; are disposed between the plurality of first and second sensing elements 72, 82. A set of sensing films 76, each sensing film among the set of sensing films 76, being disposed on a first sensing region 78 of the corresponding first sensing element 72. Nonlimiting examples of positioning of sensing films 76 include the vertical regions of the sensing elements 72, 82 and/or on the vertical regions on holes 80 in the substrate 70.

In one embodiment, sensing elements on one side of the sensor substrate 70 serve as "sensing electrodes", while sensing elements on the other side of the sensor substrate 70 serve as "reference electrodes". The use of sensing and reference electrodes provides the ability for correction for environmental instabilities such as temperature effects, or the like. Such a correction is performed when temperature affects both sensing and reference electrodes while the analyte concentration change affects only the sensing electrodes.

In another embodiment, sensing electrodes on one side of the substrate 70 operate at one resonance frequency, while sensing electrodes on the other side of the sensor substrate 70 operate at another resonance frequency. Operation of the sensing electrodes at at least two frequencies provides the ability for more selective measurements, where sensing effects at different frequencies originate from diverse interactions of the sensing film and an analyte.

Figure 16:
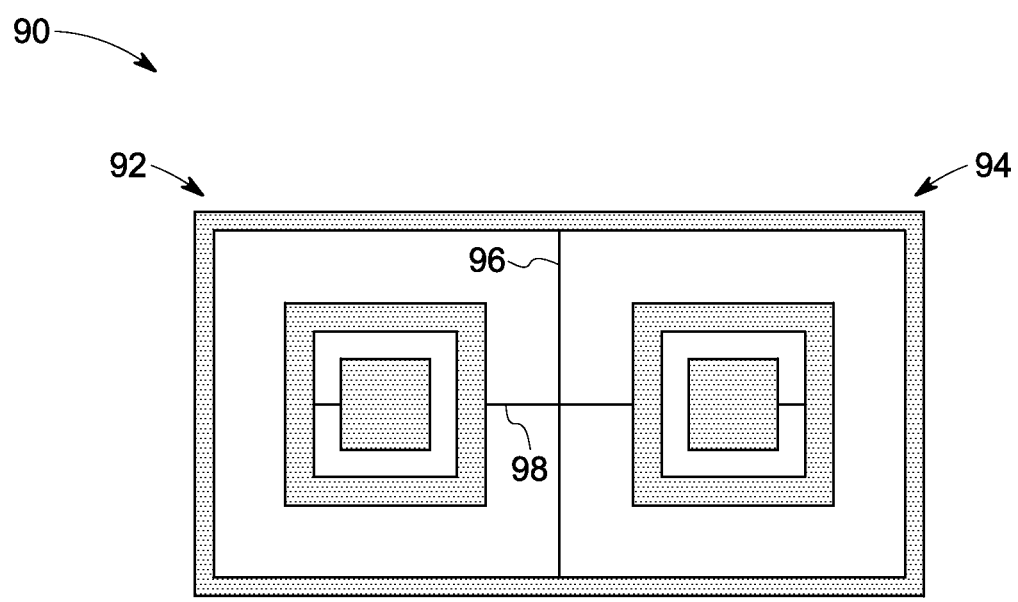
FIG. 16 is a diagrammatical representation of a split ring resonator (SRR) sensor in accordance with an exemplary embodiment of the present invention.

Referring to FIG. 16, an exemplary sensor 90 in accordance with an exemplary embodiment of the present invention is disclosed. In the illustrated embodiment, compared to FIG. 2, the sensor 90 is a split ring resonator (SRR) sensor, in particular, a dual split ring resonator sensor. The sensor 90 includes concentric split rings 92, 94 with sensing regions 96, 98. In the illustrated embodiment, the sensing regions 96, 98 are devoid of any patterns.

The electric field distribution in the sensing element is spread along the length of the sensing region. The electric field distribution in the split ring resonator structure is spread along the length of the sensing regions 96 and 98.

Figure 17:
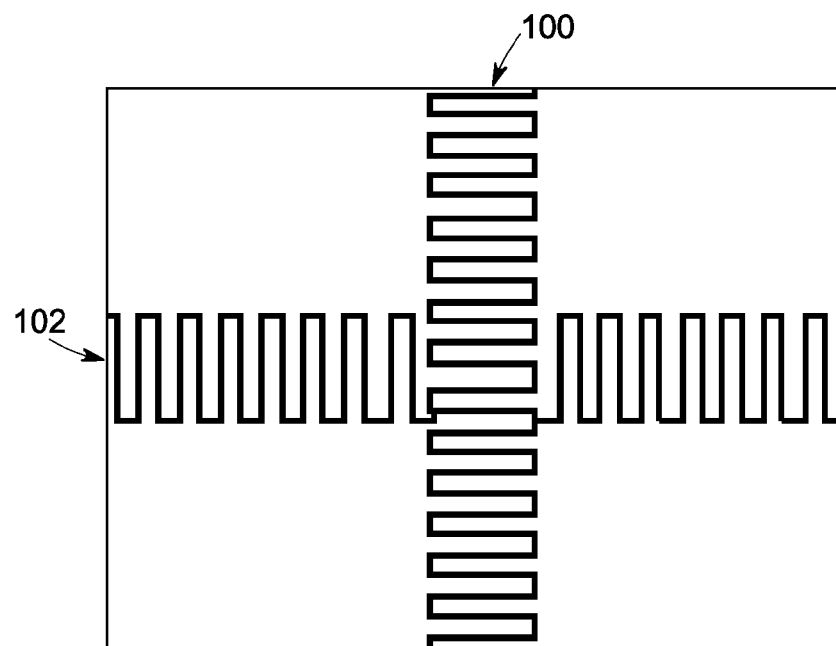
FIG. 17 is a diagrammatical representation of a split ring resonator (SRR) sensor in accordance with an exemplary embodiment of the present invention.

Referring to FIG. 17, a split ring resonator sensor in accordance with an exemplary embodiment of the present invention is disclosed. In the illustrated embodiment, the split ring resonator sensor includes sensing regions 100, 102 having meander (serpentine) shaped patterns.

Figure 18:
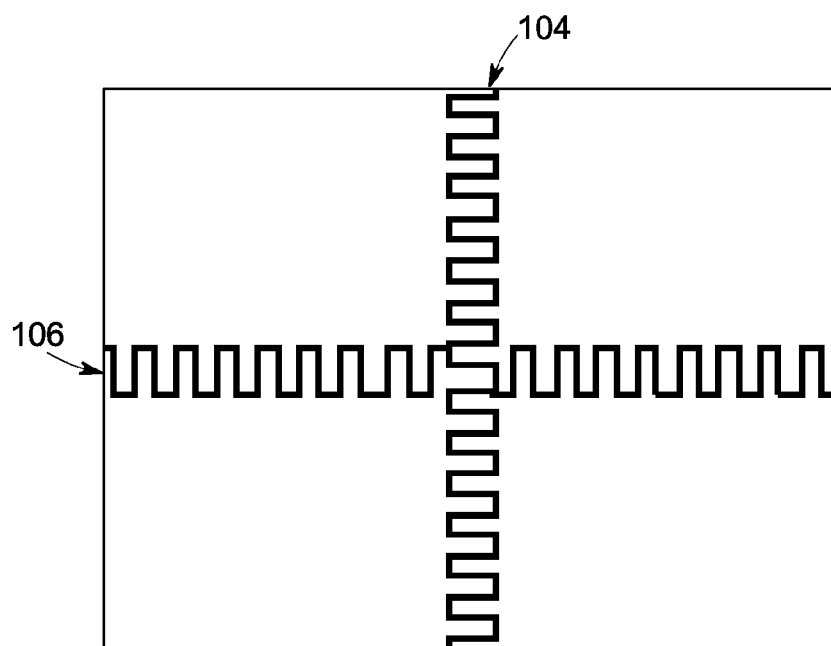
FIG. 18 is a diagrammatical representation of a split ring resonator (SRR) sensor in accordance with an exemplary embodiment of the present invention.

Referring to FIG. 18, a split ring resonator sensor in accordance with an exemplary embodiment of the present invention is disclosed. In the illustrated embodiment, the split ring resonator sensor includes sensing regions 104, 106 having meander shaped patterns. It should be noted herein that sensing regions 104, 106 having smaller cross-sectional area compared to sensing regions 100, 102 shown in FIG. 17.

Figure 19:
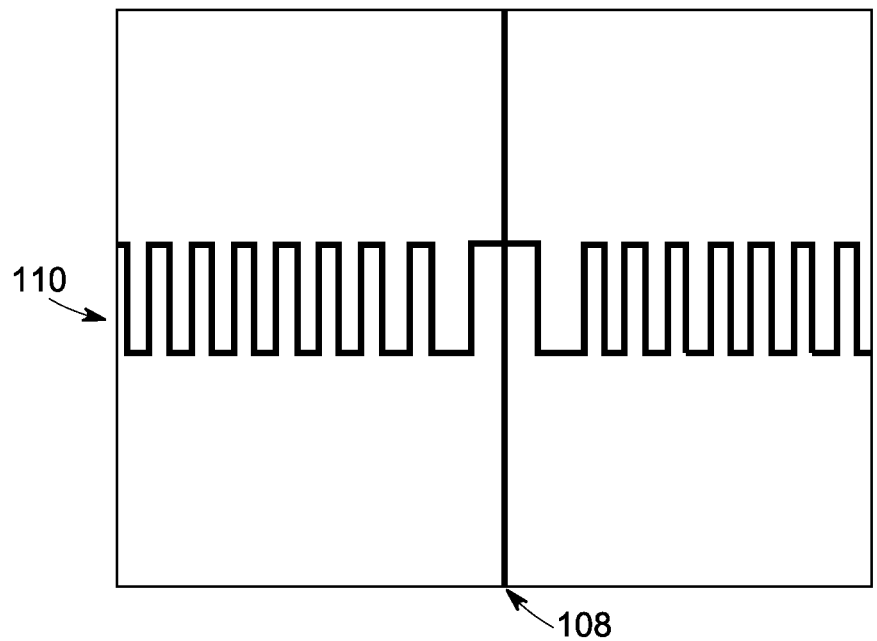
FIG. 19 is a diagrammatical representation of a split ring resonator (SRR) sensor in accordance with an exemplary embodiment of the present invention.

Referring to FIG. 19, a split ring resonator sensor in accordance with an exemplary embodiment of the present invention is disclosed. In the illustrated embodiment, the split ring resonator sensor includes sensing regions 108, 110. The sensing region 108 is devoid of patterns and the sensing region 110 has a meander shaped pattern.

Figure 20:
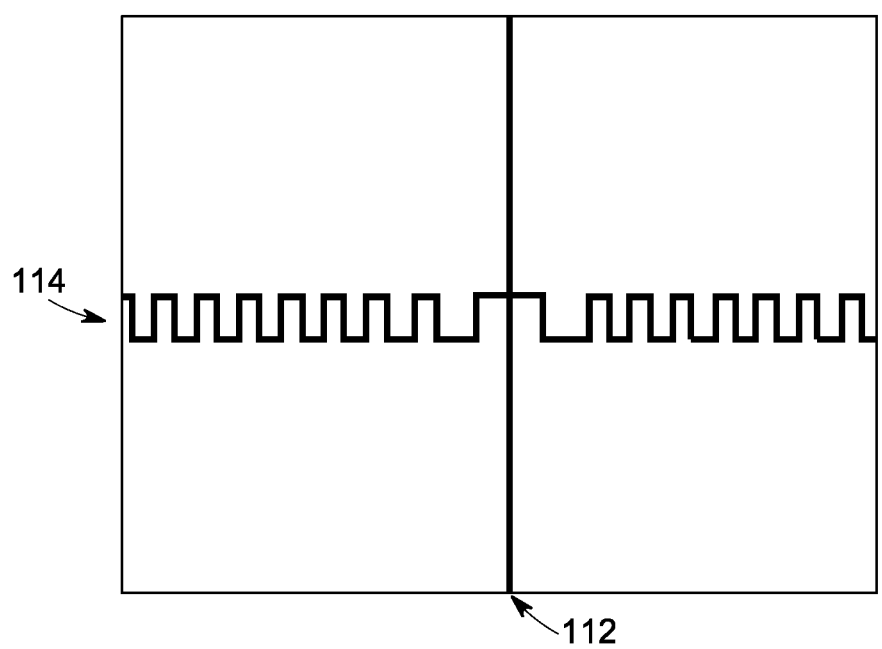
FIG. 20 is a diagrammatical representation of a split ring resonator (SRR) sensor in accordance with an exemplary embodiment of the present invention.

Referring to FIG. 20, a split ring resonator sensor in accordance with an exemplary embodiment of the present invention is disclosed. In the illustrated embodiment, the split ring resonator sensor includes sensing regions 112, 114. The sensing region 112 is devoid of patterns and the sensing region 114 has a meander shaped pattern having relatively smaller cross-sectional area.

The sensing regions of split ring resonator sensors may have different geometries with non-limiting examples of the sensing regions of resonators as shown in FIG. 16-20. The non-limiting examples of geometries of the sensing region may include straight, interdigital fingers, circular, semi-circular, or the like. The geometries provide different gap sizes, total surface area of the gap, and the ratio of the gaps in different directions. Such geometries enhance the active sensing area of the resonant sensor. It should be noted herein that the depth of field penetration is tuned by the controlled geometry.

Referring to FIG. 21, a dual-SRR (split ring resonator) sensor 116 in accordance with an exemplary embodiment of the present invention is illustrated. The SRR sensor 116 includes two pairs of sensing elements 118, 120 disposed on a dielectric substrate 122. The sensing elements 118, 120 may be fabricated by selective etching, printing, lithography, or the like. One pair of sensing elements 118 includes two concentric C-shaped conductive bands 124, 126 and the other pair of sensing elements 120 includes two concentric C-shaped conductive elements 128, 130. It should be noted herein that in each pair of sensing elements, the two concentric C-shaped conductive elements are separated from each other by a gap. The pair of sensing elements 118, 120 are separated from each other by a gap 132. The inner conductive bands 126, 130 are oriented 180 degree relative to each other. The shape of the concentric conductive bands 124, 126, 128, 130 may be rectangular, circular, diamond, hexagon, octagon, or any other shape. The pair of sensing elements 118, 120 includes openings 134, 136 respectively.

The pair of sensing elements 118, 120 are disposed facing each other. Each pair of sensing elements has a self-resonance inductance L due to the finite length of its ring structure. The dual SRR sensor 116 has a plurality of capacitive coupling areas, namely, individual gap of each conductive band, the gap between two outer conductive bands 124, 128, the gap between inner and outer conductive bands. Since each conductive band has a self-inductance and aforementioned capacitive gaps, dual-SRR operates as L-C-R (inductance-capacitance-resistance) resonating structure.

Referring to FIG. 22, the dual-SRR sensor 116 is represented as an L-C-R equivalent circuit in accordance with the embodiment of FIG. 21. The outer conductive band 124 is represented as a series R1-L1-C1, which is coupled to the inner conductive band 126 both inductively and capacitively. The inner conductive band 126 is represented as a series R3-L3-C3. The capacitive coupling between the conductive bands 124, 126 is represented as a parallel circuit R13-C13. R13 is representative of a stray resistance of the resonator sensor.

Similarly, the outer conductive band 128 is represented as a series R2-L2-C2, which is coupled to the inner conductive band 130 both inductively and capacitively. The inner conductive band 130 is represented as a series R4-L4-C4. The capacitive coupling between the conductive bands 128, 130 is represented as a parallel circuit R24-C24. Capacitive coupling between the outer conductive bands 124, 128 is represented as a parallel circuit R12-C12. It should be noted herein M1 represents inductive coupling between outer conductive bands 124, 128, M2 represents inductive coupling between conductive bands 124, 126, and M3 represents inductive coupling between conductive bands 128, 130.

The dual-SRR sensor is excited electromagnetically to create both electric and magnetic resonances. The magnetic field is perpendicular to the SRR plane, while the electric field is excited parallel to a slit of the sensor. It should be noted herein that the area of the sensor excited by the magnetic resonance is relatively smaller than the area of the sensor excited by the electric resonance case. The electric and magnetic resonances can be excited in different sensing regions of the SRR sensor. The SRR sensor may be excited in either by magnetic resonance only or by electric resonance by controlling physical geometries (slits, gaps, and distance between inner and outer conductive bands).

In one embodiment, one side of SRR sensor may be provided with a dielectric sensing film beneath, for levitating the one side of SRR sensor by swelling the sensing film. As a result, electric resonant frequency is influenced more than the magnetic resonance. In another embodiment, magnetic resonance may be separately controlled. For example, magnetic resonance may be controlled by controlling mutual inductances M2, M3. In a specific embodiment, for example, the pair of sensing elements 120 may be provided with a dielectric sensing film underneath the elements 120 for levitating one side of the sensor by swelling the sensing film so as to obtain different mutual inductances M2, M3. These different mutual inductances induce different magnetic field strength, thereby affecting the magnetic resonance more than the electric resonance.

Figure 23:
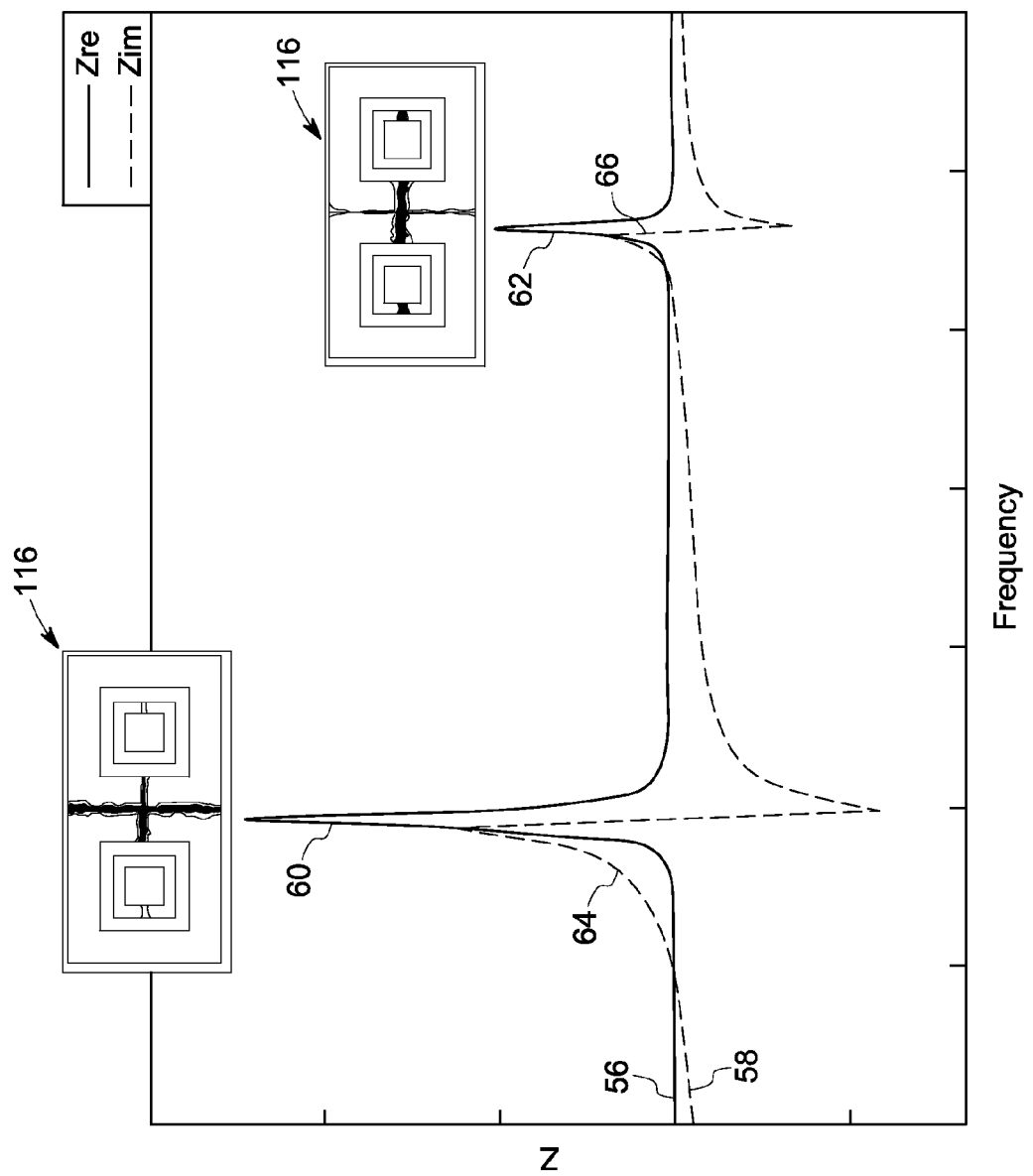
FIG. 23 is a graphical representation of a resonance impedance spectrum of an LCR sensor for measuring one or more properties of an analyte in accordance with an exemplary embodiment of the present invention.

Referring to FIG. 23, a resonance impedance spectrum of the LCR sensor for measuring one or more properties of an analyte is illustrated in accordance with an embodiment of the present invention. X-axis is represented by "frequency" of the spectrum and Y-axis is represented by "impedance" (Z) of the spectrum. The illustrated embodiment shows a curve 56 indicative of a real part (Zre) of the impedance spectrum superimposed with a curve 58 indicative of an imaginary part (Zim) of the impedance spectrum. In one embodiment, when the magnetic field is perpendicular to the plane of the split ring resonator sensor 116, while electric field is excited parallel to a slit of a split ring of the sensor 116, peak 60 may be representative of an electrical component of the real part of the impedance spectrum, and peak 62 may be representative of a magnetic component of the real part of the impedance spectrum. In another embodiment, when the magnetic field is perpendicular to the plane of the split ring resonator sensor, while the electric field is excited parallel to the gap of the split ring, peak 60 may be representative of a magnetic component of the real part of the impedance spectrum, and peak 62 may be representative of an electrical component of the real part of the impedance spectrum. Similarly, in one embodiment, peak 64 may be representative of an electrical component of the imaginary part of the impedance spectrum, and peak 66 may be representative of a magnetic component of the imaginary part of the impedance spectrum. In another embodiment, peak 64 may be representative of a magnetic component of the imaginary part of the impedance spectrum, and peak 66 may be representative of an electrical component of the imaginary part of the impedance spectrum.

The measurement of two resonances such as magnetic and electrical components provides the ability to increase the sensor response selectivity. The increase in sensor selectivity is due to the different effects of the environment on the magnetic and electrical components of the resonance spectra. In particular, the electrical component of the resonance spectrum preferentially responds to the change in the complex permittivity of the environment. The real part of the complex permittivity of the fluid is referred to as a "dielectric constant". The imaginary part of the complex permittivity of the fluid is referred to as a "dielectric loss factor". The imaginary part of the complex permittivity of the fluid is directly proportional to conductivity of fluid. The magnetic component of the resonance spectrum preferentially responds to the change in the spacing between sensing elements in the sensor structure due to swelling or shrinking of sensing films on the sensing elements.

Figure 24:
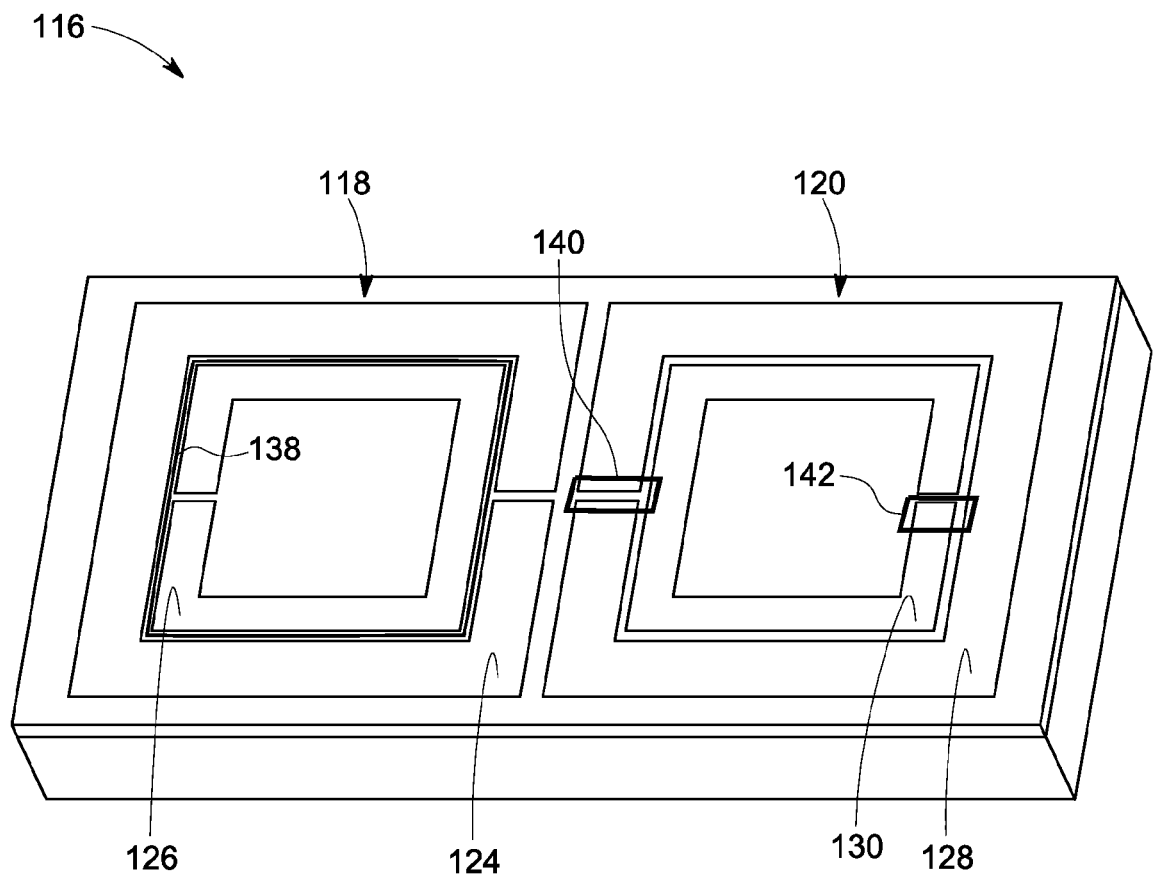
FIG. 24 is a perspective view of a dual-SRR sensor in accordance with an exemplary embodiment of the present invention.

Referring now to FIG. 24, the dual-SRR sensor 116 in accordance with an exemplary embodiment is illustrated. In the illustrated embodiment, the regions 138, 140, 142 are representative of the selective areas where different sensing films may be disposed underneath the regions to control magnetic resonance of the SRR sensor and/or inductive coupling between different regions of the SRR sensor. The sensor selectivity may be increased due to the local swelling effect of the sensing film. The selective areas may be selectively used for controlling magnetic resonance separately. In some embodiments, for example, upper or lower portion of the outer conductive bands 124, 128 may be used selectively so as to control only the slit opening of the dual-SRR sensor 116.

In FIG. 24, in one embodiment, split ring 126 of the SRR sensor 116 may be provided with a dielectric sensing film in region 138 beneath, for levitating the one side 126 of SRR sensor in relation to other side 124 of SRR sensor by swelling the sensing film. In another embodiment, split ring 128 of the SRR sensor 116 may be provided with a dielectric sensing film in region 140 beneath, for levitating the one side of the ring in relation to other side of the ring sensor by swelling the sensing film in region 140. In another embodiment, split ring 130 of the SRR sensor 116 may be provided with a dielectric sensing film in region 142 beneath, for levitating the one side of the ring in relation to other side of the ring sensor by swelling the sensing film in region 142.

In addition to above discussed dual-split ring resonator structures, aspects of the present invention may be applied to individual split ring resonators, and other LCR resonators operating at different frequency ranges including radio-frequencies, microwave frequencies, and optical frequencies, to increase sensor selectivity.

In addition to discussed dual-split ring resonator structures, the exemplary techniques for increasing sensor selectivity may be applied to individual split ring resonators, microwave split-ring resonators, radio-frequency coils, and other LCR resonators. For example, in the optical range of the electromagnetic spectrum, the resonators may be approximately in the range of 10 to 1000 nanometers in size with simplified geometries.

Figure 25:
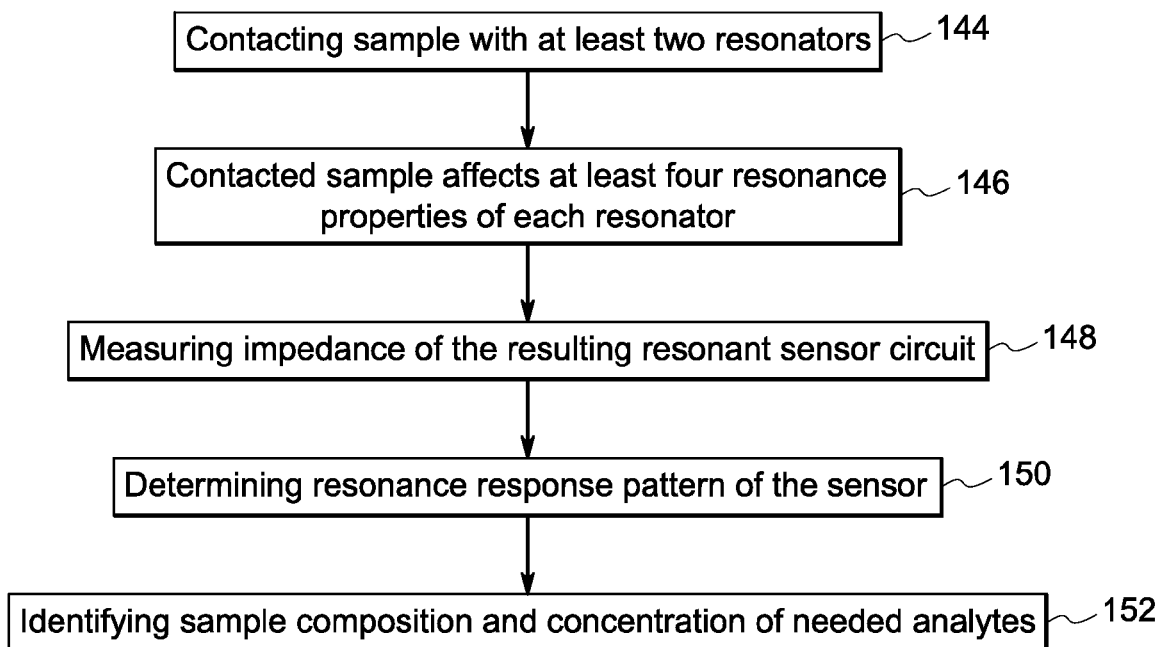
FIG. 25 is a flow chart illustrating exemplary steps involved in analyzing a sample in accordance with an exemplary embodiment of the present invention.

Referring to FIG. 25, a flow chart illustrating steps involved in analyzing a sample is disclosed. The method includes contacting an LCR sensor having at least two sensing elements, with a sample as represented by the step 144. In one embodiment, the LCR sensor includes a plurality of first sensing elements mutually spaced apart and disposed on the substrate, a plurality of second sensing elements; each second sensing element being disposed overlapping the corresponding first sensing element. An isolator is disposed between the corresponding first and second sensing elements. In a specific embodiment, the group of first and second sensing elements together form a coil structure. When a radio frequency field passes through the sensing coil structure, an AC voltage is generated across the sensing coil. In another embodiment, the sensing elements may be disposed on either sides of a substrate having a plurality of holes. In yet another embodiment, the sensing element may be a split ring resonator sensor. In another specific embodiment, the first and second sensing elements include optical LCR resonators.

In the LCR sensor, sensing response of each sensing element is provided from analyte-dependent change in circuit capacitance, analyte-dependent change in circuit resistance, analyte-dependent change in circuit inductance or a combination of the three as represented by the step 146. In other words, in accordance with the embodiments of the present technique, when the LCR sensor having at least two sensing elements coated with the same sensing material are contacted to a sample, the contacted sample affects at least four resonance properties of the sensor. The combination of changes in the capacitance, inductance, and resistance is measured by measuring frequency response spectrum of the LCR resonant sensing circuit as represented by the step 148. The analyte-induced changes in the sensing films of the sensing elements affect the impedance of the sensor circuit through the changes in circuit resistance and circuit capacitance.

The resonance response pattern of the spectrum is determined as represented by the step 150. The spectrum includes a real part (Zre) of the impedance spectrum, an imaginary part (Zim) of the impedance spectrum, frequency of the maximum of the real part of the impedance (Fp), peak magnitude of the real part of the impedance (Zp), peak frequency (F1) and magnitude (Z1) of the imaginary part of the impedance, and resonant frequency (F2) and magnitude (Z2) of the imaginary part of the impedance. The sample composition and concentration of the analyte are identified as represented by the step 152.

While only certain features of the invention have been illustrated and described herein, many modifications and changes will occur to those skilled in the art. It is, therefore, to be understood that the appended claims are intended to cover all such modifications and changes as fall within the true spirit of the invention.

The invention claimed is:

1. A sensing system for selective analyte detection in presence of interferences, comprising:
    an inductor-capacitor-resistor (LCR) resonator sensor comprising:
        a substrate;
        a plurality of first sensing elements mutually spaced apart and disposed on the substrate;
        a plurality of second sensing elements, each second sensing element disposed overlapping the corresponding first sensing element;
        at least one first sensing material film being disposed on a first sensing region of the corresponding first sensing element; and
        at least one second sensing material film being disposed on a second sensing region of the corresponding second sensing element,
        wherein at least one among the at least one first sensing material film and the at least one second material film swell resulting in modulation of an inductance of the inductor-capacitor-resistor (LCR) resonator sensor when the at least one first sensing material film and the at least one second material film interacts with an analyte.

2. The sensing system of claim 1, wherein the at least one first sensing material film and the at least one second sensing material film comprises a same type of sensing material film.

3. The sensing system of claim 1, wherein the at least one first sensing material film is a different type compared to the at least one second sensing material film.

4. The sensing system of claim 1, further comprising a plurality of dielectric isolators, each dielectric isolator being disposed between the corresponding first and second sensing elements.

5. The sensing system of claim 1, wherein the plurality of first sensing elements and the second sensing elements form a sensing coil structure.

6. The sensing system of claim 5, wherein a first end of each first sensing element is coupled to one end of the corresponding second sensing element, and a second end of each first sensing element is coupled to another end of the corresponding second sensing element.

7. The sensing system of claim 1, wherein the first sensing element is non-galvanically coupled to second sensing element.

8. The sensing system of claim 1, wherein the LCR resonator sensor further comprises a plurality of holes formed in the substrate, for enabling flow of an analyte through the holes, wherein the holes are disposed between the plurality of first sensing elements.

9. The sensing system of claim 8, wherein the LCR resonant sensor is a multivariable LCR resonant sensor; wherein an electric field distribution between the plurality of first sensing elements is substantially uniform along a plane of the plurality of first sensing elements and the holes.

10. The sensing system of claim 1, wherein the plurality of first sensing elements is disposed on a first surface of the substrate.

11. The sensing system of claim 10, wherein the LCR resonator sensor further comprises a plurality of second sensing elements disposed on a second surface opposite to the first surface of the substrate.

12. The sensing system of claim 11, further comprising a plurality of holes formed in the substrate, wherein the holes are disposed between the plurality of first sensing elements and the plurality of second sensing elements.

13. The sensing system of claim 12, further comprising at least one second sensing material film disposed on a second sensing region of the corresponding second sensing element.

14. The sensing system of claim 1, wherein the LCR resonator sensor comprises a split ring resonator sensor.

15. The sensing system of claim 14, wherein the LCR resonator sensor comprises a serpentine sensing region configured to tune electric field penetration.

16. The sensing system of claim 1, wherein the LCR resonator sensor further comprises a memory chip.

17. The sensing system of claim 1, wherein each sensing material film comprises at least one of a polymer, an organic material, an inorganic material, a biological material, a nanomaterial, a nanocomposite material, and a colloidal crystal material.

18. The sensing system of claim 1, wherein the sensing system is used for measurement of at least one of physical, chemical, and biological properties of analyte.

19. A method for measuring one or more conditions of a sample, the method comprising:
    transmitting an electromagnetic signal from an inductor-capacitor-resistor (LCR) resonator sensor; wherein the LCR resonator sensor comprises a substrate; a plurality of first sensing elements mutually spaced apart and disposed on the substrate; a plurality of second sensing elements, each second sensing element disposed overlapping the corresponding first sensing element; at least one first sensing material film being disposed on a first sensing region of the corresponding first sensing element, and at least one second sensing material film being disposed on a second sensing region of the corresponding second sensing element; and
    sensing the LCR resonator sensor signal via a detector,
    wherein at least one among the at least one first sensing material film and the at least one second material film swell resulting in modulation of an inductance of the inductor-capacitor-resistor (LCR) resonator sensor when the at least one first sensing material film and the at least one second material film interacts with the sample.

20. The method of claim 19, wherein the step of sensing comprises determining impedance spectrum of the at least one first sensing material film, the at least one second sensing material film and calculating dielectric change based on the impedance spectrum, using multivariate analysis.

21. A method for fabrication of an inductor-capacitor-resistor (LCR) resonator sensor, comprising:
    applying a plurality of first sensing elements on a substrate;
    applying at least one dielectric layer on the plurality of first sensing elements; and applying a plurality of second sensing elements on the at least one dielectric layer, each second sensing element being disposed corresponding to position of each first sensing element such that the at least one dielectric layer is disposed between the first and second sensing elements; wherein shape of the substrate does not change during fabrication;

disposing at least one first sensing material film on a first sensing region of the corresponding first sensing element; and disposing at least one second sensing material film on a second sensing region of the corresponding second sensing element, wherein at least one among the at least one first sensing material film and the at least one second material film swell resulting in modulation of an inductance of the inductor-capacitor-resistor (LCR) resonator sensor when the at least one first sensing material film and the at least one second material film interacts with an analyte.

22. The method of claim 21, wherein the at least one dielectric layer has a thickness in a range of one to five thousand nanometers.

23. A method for fabrication of an inductor-capacitor-resistor (LCR) resonator sensor, comprising:

applying a plurality of first sensing elements on a substrate;

applying at least one dielectric layer on the plurality of first sensing elements, and applying a plurality of second sensing elements on the at least one dielectric layer, each second sensing element being disposed corresponding to position of each first sensing element such that the at least one dielectric layer is disposed between the plurality of first and second sensing elements;

removing a portion of dielectric layer to form a horizontal gap between the plurality of first and second sensing elements; wherein shape of the substrate does not change during fabrication;

disposing at least one first sensing material film on a first sensing region of the corresponding first sensing element; and disposing at least one second sensing material film on a second sensing region of the corresponding second sensing element, wherein at least one among the at least one first sensing material film and the at least one second material film swell resulting in modulation of an inductance of the inductor-capacitor-resistor (LCR) resonator sensor when the at least one first sensing material film and the at least one second material film interacts with an analyte.

24. The method of claim 23, wherein the gap is a sensing region.

25. The method of claim 23, wherein the LCR resonant sensor is a multivariable LCR resonant sensor.

26. The method of claim 25, wherein the at least one dielectric layer has a thickness in a range of one to five thousand nanometers.

27. The method of claim 23, wherein the gap is in the range of one nanometer to thousand nanometers.

28. The method of claim 23, wherein the gap is in the range of one micrometer to thousand micrometers.

29. The method of claim 23, wherein the gap is in the range of one nanometer to thousand micrometers.

30. The method of claim 23, wherein the gap is in the range of one nanometer to thousand nanometers.

* * * * *